(12) United States Patent
McKenna

(10) Patent No.: US 10,410,741 B1
(45) Date of Patent: Sep. 10, 2019

(54) FOOT PRINTING SYSTEMS AND METHODS OF UTILIZING THEREOF

(71) Applicant: CertaScan Technologies, LLC, Fairfield, CT (US)

(72) Inventor: James B. McKenna, Fairfield, CT (US)

(73) Assignee: CertaScan Technologies, LLC, Fairfield, CT (US)

( * ) Notice: Subject to any disclaimer, the term of this patent is extended or adjusted under 35 U.S.C. 154(b) by 785 days.

(21) Appl. No.: 14/616,070

(22) Filed: Feb. 6, 2015

Related U.S. Application Data

(60) Provisional application No. 61/936,724, filed on Feb. 6, 2014, provisional application No. 62/073,115, filed on Oct. 31, 2014.

(51) Int. Cl.
| | |
|---|---|
| *G16H 10/60* | (2018.01) |
| *G06K 9/00* | (2006.01) |
| *H04N 7/18* | (2006.01) |

(52) U.S. Cl.
CPC ......... *G16H 10/60* (2018.01); *G06K 9/00013* (2013.01); *H04N 7/18* (2013.01)

(58) Field of Classification Search
None
See application file for complete search history.

(56) References Cited

U.S. PATENT DOCUMENTS

| | | | | |
|---|---|---|---|---|
| 1,861,367 A | * | 5/1932 | Smith | A61B 5/1172 118/31.5 |
| 2005/0099619 A1 | * | 5/2005 | McClurg | G06K 9/00046 356/71 |
| 2011/0200236 A1 | * | 8/2011 | Roemen | A61B 5/1172 382/124 |
| 2015/0348174 A1 | * | 12/2015 | Purvis, Jr. | G06F 16/51 705/26.5 |

* cited by examiner

*Primary Examiner* — Michael Tomaszewski
(74) *Attorney, Agent, or Firm* — Greenberg Traurig, LLP

(57) ABSTRACT

In some embodiments, the instant invention provides for a computer system, including: 1) a specialized scanner; 2) a server having software stored in a computer readable medium accessible by the server; where the software is configured to: i) receive: a) forensic quality images of the foot print of the infant, b) the forensic quality image of the finger print of the mother; and c) an identification parameter of the mother ii) generate a customer identification number and correlate the customer identification number with: a) the forensic quality images of the foot print of the infant, b) the forensic quality image of the finger print of the mother; and c) the input of the identification parameter of the mother; iii) select a sharpest forensic quality image; iv) store: the sharpest forensic quality image, iv) create a correlation, v) generate an output, and 3) a plurality of specifically programmed input/output devices.

14 Claims, 35 Drawing Sheets

Mom's Information:

First Name
Last Name
Email
OR
Street Address
City
State
Zip

Baby's Information:

First Name
Middle Name
DOB
Time        AM/PM
Lbs         Ounces
Length
Sex

BACK

NEXT

*FIG. 6*

Parent Confirmation Screen- Nurse to confirm prior to capturing foot prints

Please confirm that you will be creating a foot print record for the following patient's baby:

First Name

Last Name

BACK        CONTINUE

*FIG. 7*

Please wait while foot prints and mom's information are merged

FOOT PRINTING SYSTEMS AND METHODS OF UTILIZING THEREOF

RELATED APPLICATIONS

This application claims the priority of U.S. provisional application U.S. Patent Appln. No. 61/936,724; filed Feb. 6, 2014; entitled "FOOT PRINTING SYSTEMS AND METHODS OF UTILIZING THEREOF," and U.S. provisional application U.S. Patent Appln. 62/073,115; filed Oct. 31, 2014; entitled "FOOT PRINTING SYSTEMS AND METHODS OF UTILIZING THEREOF" which are incorporated herein by reference in their entireties for all purposes.

TECHNICAL FIELD

In some embodiments, the instant invention is related to computer methods/systems to scan and generate at least one footprint.

BACKGROUND

In most hospitals in the United States, a birth certificate is typically issued and includes the footprints of the newborn. However, in recent years, the print media and scientific journals have expressed the opinion that hospitals waste time and money by foot-printing newborns because of its poor reliability. Foot-printing of newborns is accurate less than 20% of the time.

SUMMARY OF INVENTION

In some embodiments, the instant invention provides for a computer system, including: 1) a specialized scanner designed to capture: i) a plurality of forensic quality images of at least one foot print of an infant within a second, and ii) at least one forensic quality image of at least one finger print of a mother, where the forensic quality images have a forensic quality that is achieved when: at least 80% of the plurality of forensic quality images have a gray-scale dynamic range of at least 200 gray-levels, and at least 99% of the plurality of forensic quality images have a dynamic range of at least 128 gray-levels; 2) at least one server having software stored in a computer readable medium accessible by the at least one server; where the software is at least configured to: i) receive, in real-time: a) the plurality of the forensic quality images of the at least one foot print of the infant captured by the specialized scanner, b) the at least one forensic quality image of the at least one finger print of the mother captured by the specialized scanner; and c) at least one identification parameter of the mother; ii) generate, in real-time, at least one customer identification number and correlate, in real-time, the at least one customer identification number with: a) the plurality of forensic quality image of the at least one foot print of the infant captured by the specialized scanner, b) the at least one forensic quality image of the at least one finger print of the mother captured by the specialized scanner; and c) the input of the at least one identification parameter of the mother; iii) select, in real-time, at least one sharpest forensic quality image of the at least one foot print of the infant from the plurality of forensic quality image of the at least one foot print of the infant captured by the specialized scanner; iv) store, in real-time, in at least one database accessible by the at least one server, in real-time: a) the at least one sharpest forensic quality image of the at least one foot print of the infant captured by the specialized scanner, b) the at least one forensic quality image of the at least one finger print of the mother captured by the specialized scanner, and c) the at least one identification parameter of the mother and the at least one customer identification number; iv) create, in real-time, a correlation, in the at least one database, between the at least one sharpest forensic quality image of the at least one foot print of the infant and the at least one forensic quality image of the at least one finger print of the mother; v) generate at least one output based, at least in part, on the correlation between the at least one sharpest forensic quality image of the at least one foot print of the infant and the at least one forensic quality image of the at least one finger print of the mother; and 3) a plurality of specifically programmed input/output devices, where each specifically programmed input device is configured to: i) receive, in real-time, for each infant having at least one respective sharpest forensic quality image stored in the at least one database, at least one command input wherein the at least one command input has at least one of: at least one particular identification parameter and the at least one particular customer identification number; ii) retrieve, in real-time, at least one particular sharpest forensic quality image of the at least one foot print of the infant from the at least one database; and iii) display, in real-time, the at least one particular sharpest forensic quality image of the at least one foot print of the infant; where the at least one server, the at least one database and the plurality of specifically programmed input devices communicate through a computer network.

In some embodiments, the system further includes a specifically programmed printer configured to produce hardcopy images, where the hardcopy images maintain sharpness and detail rendition structure up to at least 4× magnification.

In some embodiments, the system is configured to electronically compare at least one first forensic quality image of at least one first foot print of the infant captured by the specialized scanner at a first time point with at least one second forensic quality image of at the least one second foot print of the infant captured by the specialized scanner captured at a second time point to determine the at least one sharpest forensic quality image of the at least one foot print of the infant.

In some embodiments, the system is further configured to: for each forensic quality image of the at least one foot print of the infant, extract, in real-time, ridge detail within a predetermined area of such forensic quality image, creating, in real-time, at least one topographic representation of such forensic quality image based, at least in part, on ridge detail; and matching, in real-time, the at least one topographic representation of such forensic quality image of the at least one foot print of the infant to at least one other topographic representation of at least one other image of at least one other foot print of at least one other infant.

In some embodiments, the at least one identification parameter includes: at least one email address of the mother, at least one cell phone number of the mother, at least one home phone number of the mother, at least one address of the mother, at least one password provided by the mother, or any combination thereof.

In some embodiments, the output is at least one of: at least one printout, at least one graphical image shown on a graphical user interface of at least one specifically programmed input/output device, and any combination thereof. In some embodiments, the at least one printout is a keepsake personalized with information related to a facility in which the infant has been delivered. In some embodiments, the software is further configured to: encrypt and decrypt, in real-time, communications between the at least one server, the at least one database and the plurality of specifically programmed input devices. In some embodiments, the plurality of specifically programmed input devices are at least a thousand of specifically programmed input devices; and where the at least one server is configured to manage, in real-time, the at least a thousand of specifically programmed input devices.

In some embodiments, the instant invention provides for a computer method, including: 1) capturing by use of a specialized scanner: i) a plurality of forensic quality images of at least one foot print of an infant within a second, and ii) at least one forensic quality image of at least one finger print of a mother, where the forensic quality images have a forensic quality that is achieved when: at least 80% of the plurality of forensic quality images have a gray-scale dynamic range of at least 200 gray-levels, and at least 99% of the plurality of forensic quality images have a dynamic range of at least 128 gray-levels; 2) receiving, in real-time: a) the plurality of the forensic quality images of the at least one foot print of the infant captured by the specialized scanner, b) the at least one forensic quality image of the at least one finger print of the mother captured by the specialized scanner; and c) at least one identification parameter of the mother; 3) generating, in real-time, at least one customer identification number and correlating, in real-time, the at least one customer identification number with: a) the plurality of forensic quality image of the at least one foot print of the infant captured by the specialized scanner, b) the at least one forensic quality image of the at least one finger print of the mother captured by the specialized scanner; and c) the input of the at least one identification parameter of the mother; 4) selecting, in real-time, at least one sharpest forensic quality image of the at least one foot print of the infant from the plurality of forensic quality image of the at least one foot print of the infant captured by the specialized scanner; 5) storing, in real-time, in at least one database accessible by the at least one server, in real-time: a) the at least one sharpest forensic quality image of the at least one foot print of the infant captured by the specialized scanner, b) the at least one forensic quality image of the at least one finger print of the mother captured by the specialized scanner, and c) the at least one identification parameter of the mother and the at least one customer identification number; 6) creating, in real-time, a correlation, in the at least one database, between the at least one sharpest forensic quality image of the at least one foot print of the infant and the at least one forensic quality image of the at least one finger print of the mother; 7) generating at least one output based, at least in part, on the correlation between the at least one sharpest forensic quality image of the at least one foot print of the infant and the at least one forensic quality image of the at least one finger print of the mother; 8) receiving, by a plurality of specifically programmed input/output devices, in real-time, for each infant having at least one respective sharpest forensic quality image stored in the at least one database, at least one command input wherein the at least one command input has at least one of: at least one particular identification parameter and the at least one particular customer identification number; 9) retrieving, by a plurality of specifically programmed input/output devices, in real-time, at least one particular sharpest forensic quality image of the at least one foot print of the infant from the at least one database; and 10) displaying, by a plurality of specifically programmed input/output devices, in real-time, the at least one particular sharpest forensic quality image of the at least one foot print of the infant.

In some embodiments, the method further includes: producing hardcopy images by use of a specifically programmed printer, where the hardcopy images maintain sharpness and detail rendition structure up to at least 4× magnification. In some embodiments, the method further includes electronically comparing at least one first forensic quality image of at least one first foot print of the infant captured by the specialized scanner at a first time point with at least one second forensic quality image of at the least one second foot print of the infant captured by the specialized scanner captured at a second time point to determine the at least one sharpest forensic quality image of the at least one foot print of the infant.

In some embodiments, the method further includes: extracting, in real-time, for each forensic quality image of the at least one foot print of the infant, ridge detail within a predetermined area of such forensic quality image, creating, in real-time, at least one topographic representation of such forensic quality image based, at least in part, on ridge detail; and matching, in real-time, the at least one topographic representation of such forensic quality image of the at least one foot print of the infant to at least one other topographic representation of at least one other image of at least one other foot print of at least one other infant.

In some embodiments, the at least one identification parameter includes: at least one email address of the mother, at least one cell phone number of the mother, at least one home phone number of the mother, at least one address of the mother, at least one password provided by the mother, or any combination thereof. In some embodiments, the output is at least one of: at least one printout, at least one graphical image shown on a graphical user interface of at least one specifically programmed input/output device, and any combination thereof. In some embodiments, the at least one printout is a keepsake personalized with information related to a facility in which the infant has been delivered.

In some embodiments, the method further includes: encrypting and decrypting, in real-time, communications between the at least one server, the at least one database and the plurality of specifically programmed input devices.

In some embodiments, the plurality of specifically programmed input devices are at least a thousand of specifically programmed input devices; and where the at least one server is configured to manage, in real-time, the at least a thousand of specifically programmed input devices.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIGS. 6-10 illustrate some embodiments of the system of the present invention, showing interfaces for providing at least one user to input selected data.

Figure 1:
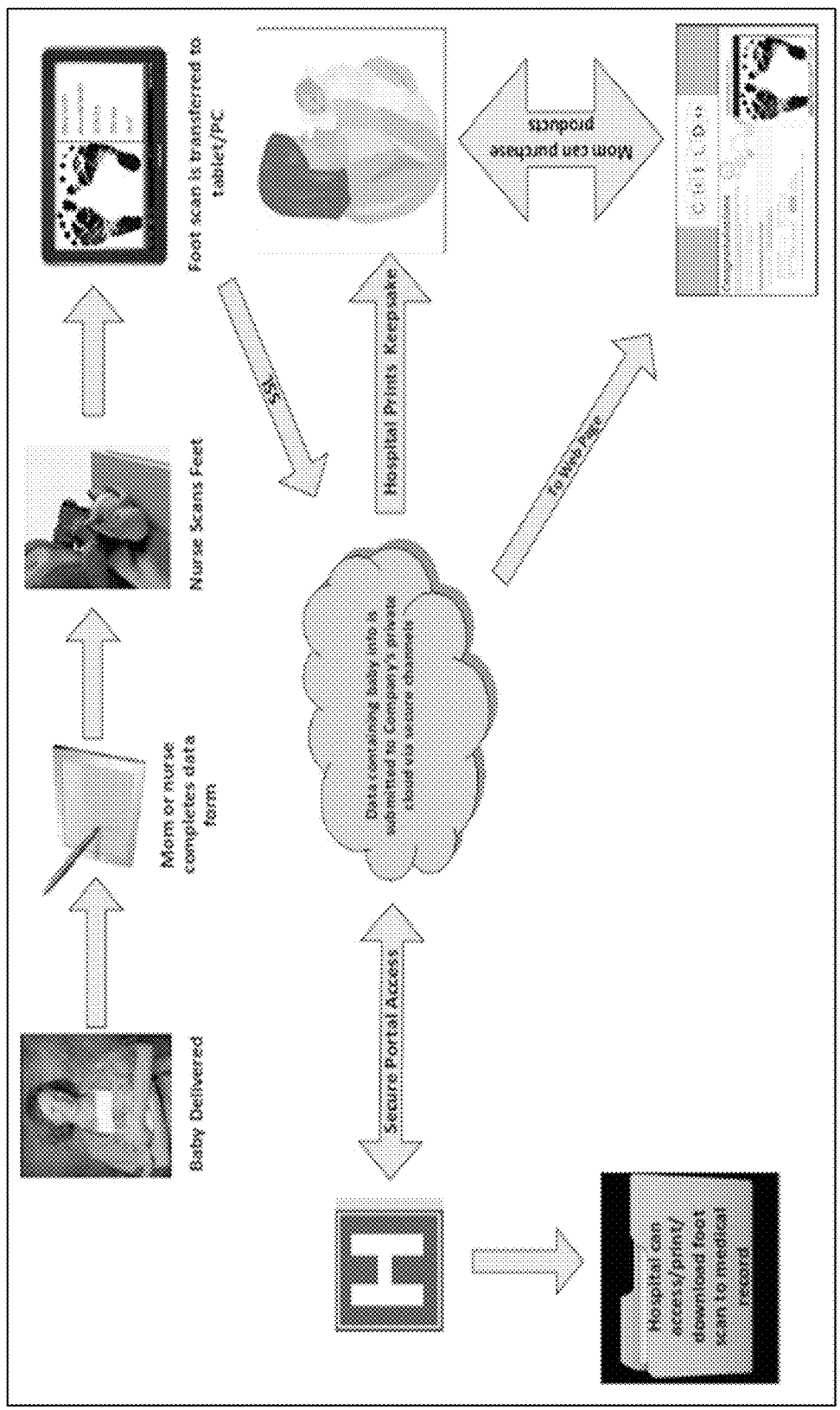
FIG. 1 illustrates some embodiments of the system of the present invention, showing data containing information of a newborn being communicated in a network.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

DESCRIPTION OF EXEMPLARY EMBODIMENTS

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the description, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and dynamically. As used herein, the term "real-time" means that an event/action can occur instantaneously or almost instantaneously in time when another event/action has occurred.

As used herein, the term "dynamic(ly)" means that an event/action that can occur without any human intervention. The event/action may be in real-time and/or hourly, daily, weekly, monthly, annually, etc.

In one example, the instant invention allows to address the problem that about 65% of US hospitals still use ink or inkless paper methods for foot printing infants which due to its ineffectiveness for identification it has devolved into a mere keepsake for parents.

In some embodiments, the specifically programmed newborn foot printing systems of the instant invention and the methods of utilizing them allow to provide a digital solution that can be used in for all born infants. In some embodiments, the specifically programmed newborn foot printing systems of the instant invention and the methods of utilizing them allow to digitally capture and unique identification each newborn (e.g., the critical friction ridge minutiae). For example, the instant invention allows hospitals to track newborns with certainty, from the time of birth and throughout their stay.

In some embodiments, the specifically programmed newborn foot printing systems of the instant invention and the methods of utilizing them allow to ensure efficient and usable capture of newborn foot images for identification, security and/or parent assurance. For example, the instant invention allows hospitals to be more compliant due to rapid (e.g., 5 minutes or less to footprint a newborn) and easier process (e.g., no paper, no ink), and the clarity of foot scan for effective identification.

In some embodiments, the specifically programmed foot printing systems of the instant invention and the methods of utilizing them allow to capture high resolution, forensic quality footprints (e.g., but not limited to, the inventive scans meet the image quality standard (IQS) set in Appendix F of FBI's Criminal Justice Information Services' regulation IAFIS-DOC-01078-9.1, which is hereby incorporated by reference therein) for various purposes (e.g., hospital/medical records, police records, etc.).

In some embodiments, the specifically programmed foot printing systems of the instant invention utilize specialized scanning equipment such as the 3M Cogent CS500e scanner whose description of functions and characteristics is hereby incorporated by reference herein to illustrate an example of suitable scanners.

In some embodiments, the specifically programmed foot printing systems of the instant invention utilize specialized scanning equipment such as the Patrol ID Identification Flats system by Cross Match Technologies, Inc., whose description of functions and characteristics is hereby incorporated by reference herein to illustrate another example of suitable scanners. In some embodiments, the specifically programmed foot printing systems of the instant invention utilize can utilize specifically programmed smart mobile portable devices (e.g., smartphones, tablets, etc.) for scanning a foot to result in a footprint.

In some embodiments, the specifically programmed newborn foot printing systems of the instant invention and the methods of utilizing them allow to capture child's (e.g., newborn) footprint(s) together with a finger and/or footprint(s) of family member/custodian (e.g., mother, father, etc.). In some embodiments, recording footprints of each child/infant (e.g., at admission/re-admissions to pediatrics), by itself or along with the mother's fingerprint (e.g., right index finger) can reduce identity fraud.

In some embodiments, the specifically programmed newborn foot printing systems of the instant invention and the methods of utilizing them allow medical professionals to scan newborn's feet and capture key data on baby or baby and family member(s)/custodian(s) (e.g., mother, father, sibling, etc.).

In some embodiments, the specifically programmed foot printing systems of the instant invention and the methods of utilizing them allow to electronically compare footprint images of the same individual (e.g., newborn, child, adult) at different times (e.g., at different ages) to confirm and/or track individual's identity based on electronically verifiable unique details of each footprint. For example, FIGS. 34A and 34B illustrate an embodiment of the inventive system which is configured to conduct an algorithmic search in a footprint databased to find a match based on at least one reference print section (e.g., 1 centimeter×1 centimeter). In some embodiments, the specifically programmed newborn foot printing systems of the instant invention can utilize suitable type of scanning algorithm(s) such as a topographic ground scanning algorithm employed by satellites (e.g., Depart Of Defense satellites). For example, in some embodiments, the specifically programmed newborn foot printing systems of the instant invention utilize a topographic ground scanning algorithm of Sciometrics LLC, Herndon, Va. (http://sciometrics.com) that can involve (as, for example, illustrated by FIGS. 33-34B), but not limited to:

applying a mask to a foot print that extracts ridge detail and converts to a digital version of the footprint as a topographic representation, and extracting a sample area of adequate detail which can be used to compare to other prints within a footprint database (e.g., that sample area can be as small as 1 cm×1 cm).

In some embodiments, the specifically programmed newborn foot printing systems of the instant invention and the methods of utilizing them allow to process payments for foot printing based on: the scan-basis (e.g., a fee per scan, a fee per a group of scans, etc.); time-basis (e.g., a number of scans per time period); membership-basis, access-basis, advertisement-basis, and/or any other similarly suitable basis. For example, relevant professionals/institutions/companies (e.g., hospitals, midwives, police, insurance companies, etc.) can pay to an operator of the specifically programmed newborn foot printing system of the instant invention a fee per scan. For example, moms can pay for keepsakes (such as one shown in FIG. 3) beyond what hospitals will provide for free. For example, marketers can pay for: advertisements to reach mom market, data analytics, etc.

In some embodiments, the specifically programmed newborn foot printing systems of the instant invention and the methods of utilizing them allow for a mom to access a baby's footprints through use of a secure web portal, where the secure web portal is configured to require the following: the mom's email address, cell phone number, home phone number, a home address, a password previously provided to/by the mom, a unique 13 digit customer identification number, or any combination thereof.

In some embodiments, the specifically programmed foot printing systems of the instant invention and the methods of utilizing them allow to encrypt the capture data (e.g., scans, personal information, etc.) by various suitable encryption techniques, such as, but not limited to, symmetric key encryption and public key encryption. For example, some embodiments utilize encryption protocol(s) that meet the Federal Information Process Standard (FIPS) 140-2 encryption and/or HIPAA standard. For example, some embodiments can utilize the PGP Hybrid Cryptographic Optimizer (HCO) technology. For example, some embodiments utilize encryption protocol(s) that meet the HITECH standard. In some embodiments, the data storage meets the requirements of the SOC-1 (SSAE-16) Reporting Standard.

In addition to encryption, in some embodiments, the specifically programmed foot printing systems of the instant invention and the methods of utilizing them further include various verification techniques to protect the integrity and authenticity of the transmitted and/or stored data. For example, in some embodiments, the instant invention utilizes a message authentication code (MAC) and/or a digital signature to protect the integrity and authenticity of the data.

In some embodiments, the specifically programmed foot printing systems of the instant invention and the methods of utilizing them are configured to utilize a low voltage light emitting diode(s) ("LED") optical technology to obtain a high resolution (e.g., 500 dots per inch (DPI)) image of the ridges on a sample, e.g., a foot. In some embodiments, the inventive systems of the instant invention provide a user a real-time image and/or automatically obtains the highest quality images(s) (i.e., sharpest image) during a scan (e.g., a 1, 2, 3, 4, 5, 6, 7, 8, 9, 10, etc. images per the second scan). In some embodiments, during, e.g., a 2 second scan, 32 images can be obtained and/or compared and the inventive system can be configured to select the sharpest image. In some embodiments, the inventive system can be configured to obtain at least one image that is about 1.5 megabytes (Mb) in size and/or combine the at least one image with any additional information/data obtained (e.g., identification information, such as name/age/gender of baby and/or parent(s)) to generate a file of a size, e.g., about 3.5 Mb.

In some embodiments, the specifically programmed foot printing systems of the instant invention and the methods of utilizing them can generate a keepsake (e.g., can be co-branded with hospital information), can print at least one copy (e.g., 2, 3, 4, 5, 6, 7, 8, 9, 10, etc.), can generate a unique 13 digit customer ID#, can condense the file(s) (i.e., zip the files), can prepare the file(s), can transmit the file(s) securely, or any combination thereof.

FIG. 1 shows a screenshot of an illustrative flowchart in accordance with some embodiments of the instant invention.

Figure 2:
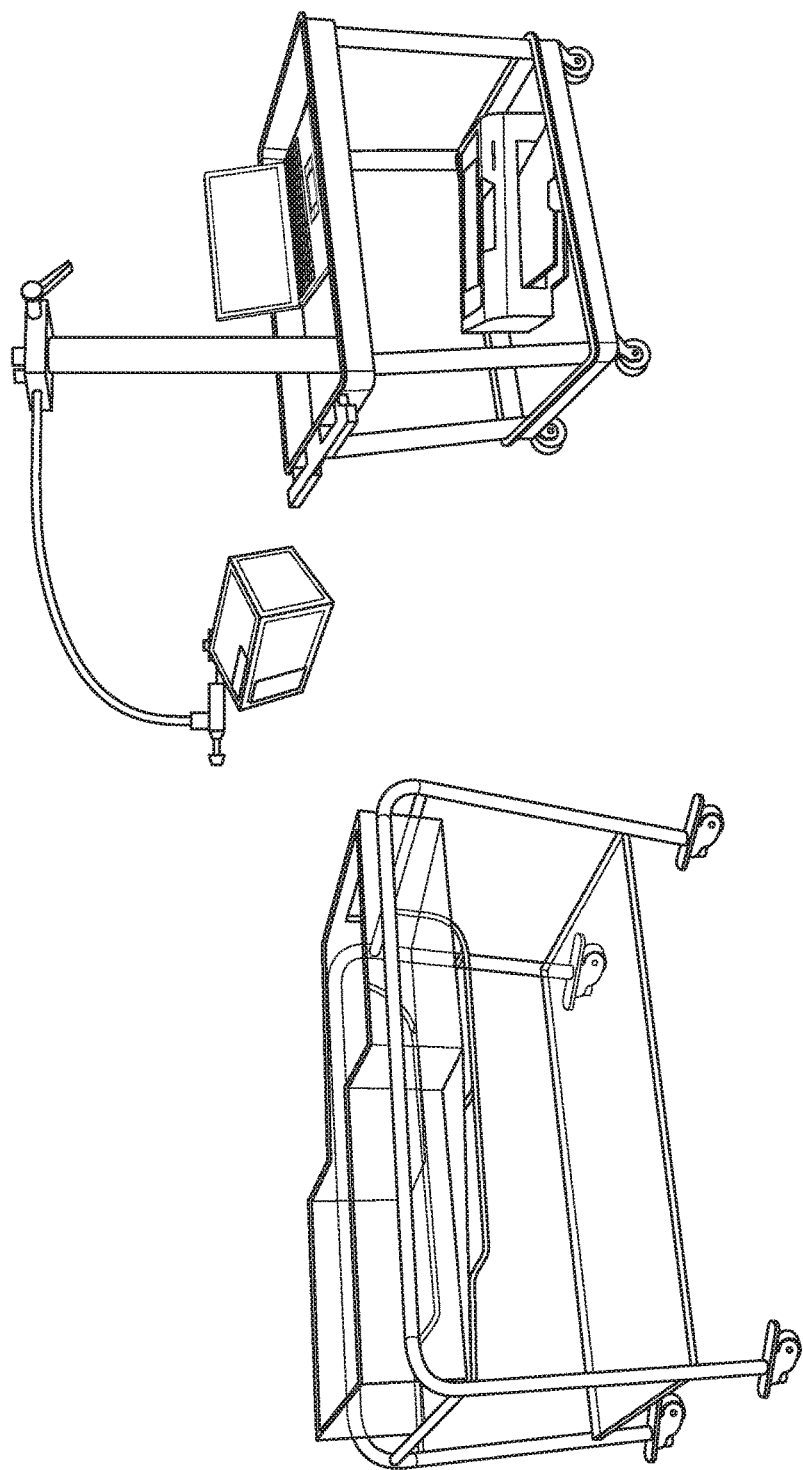
FIG. 2 illustrates some embodiments of the system of the present invention, showing a set-up of the system including a specialized scanner.

FIG. 2 shows a screenshot of an illustrative embodiment of the exemplary foot printing system of the instant invention.

Figure 3:
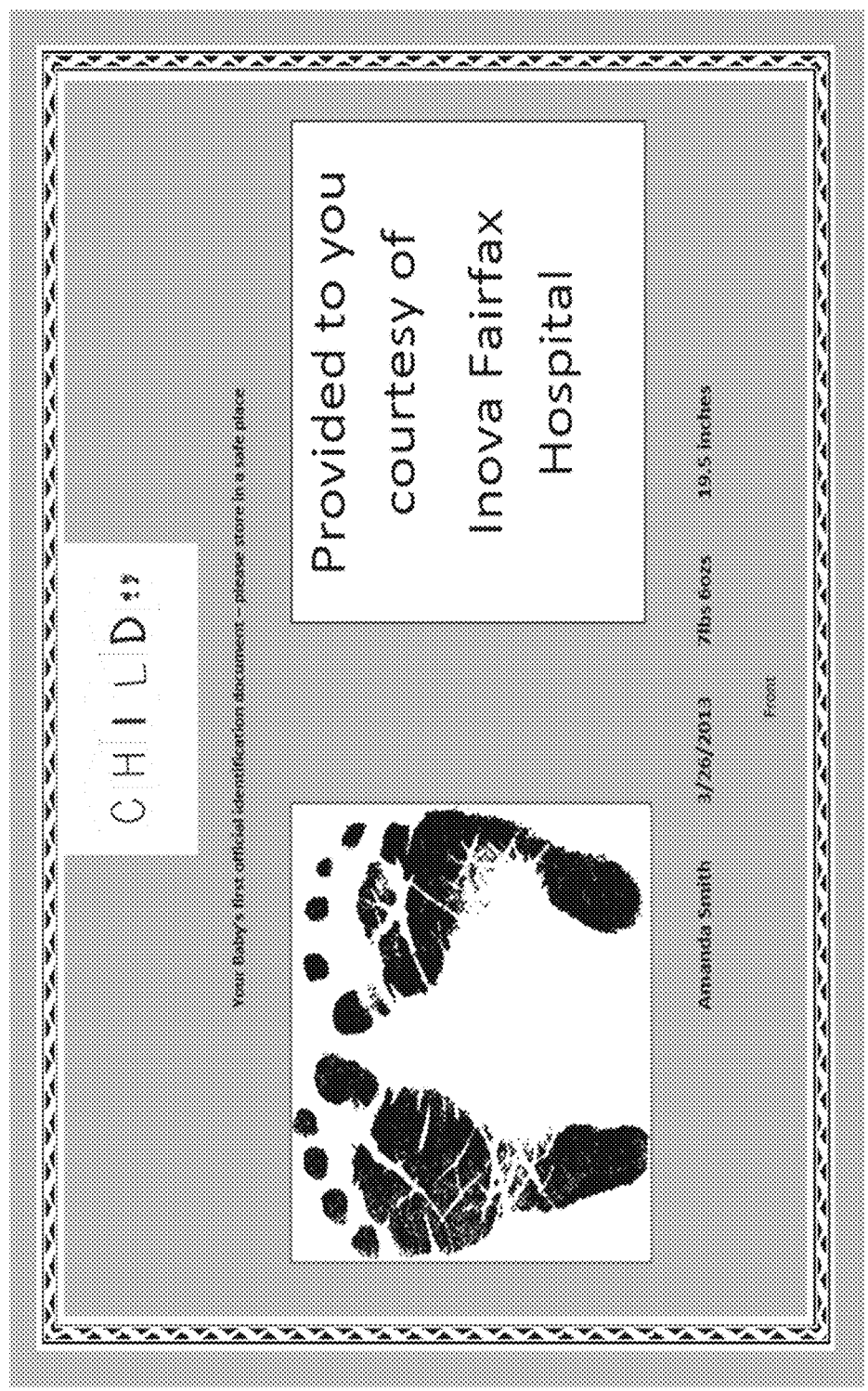
FIG. 3 illustrates some embodiments of the system of the present invention, showing an image of footprints generated by the inventive system.

FIG. 3 shows a screenshot of an illustrative keepsake generated by the exemplary foot printing system of the instant invention.

Figure 4:
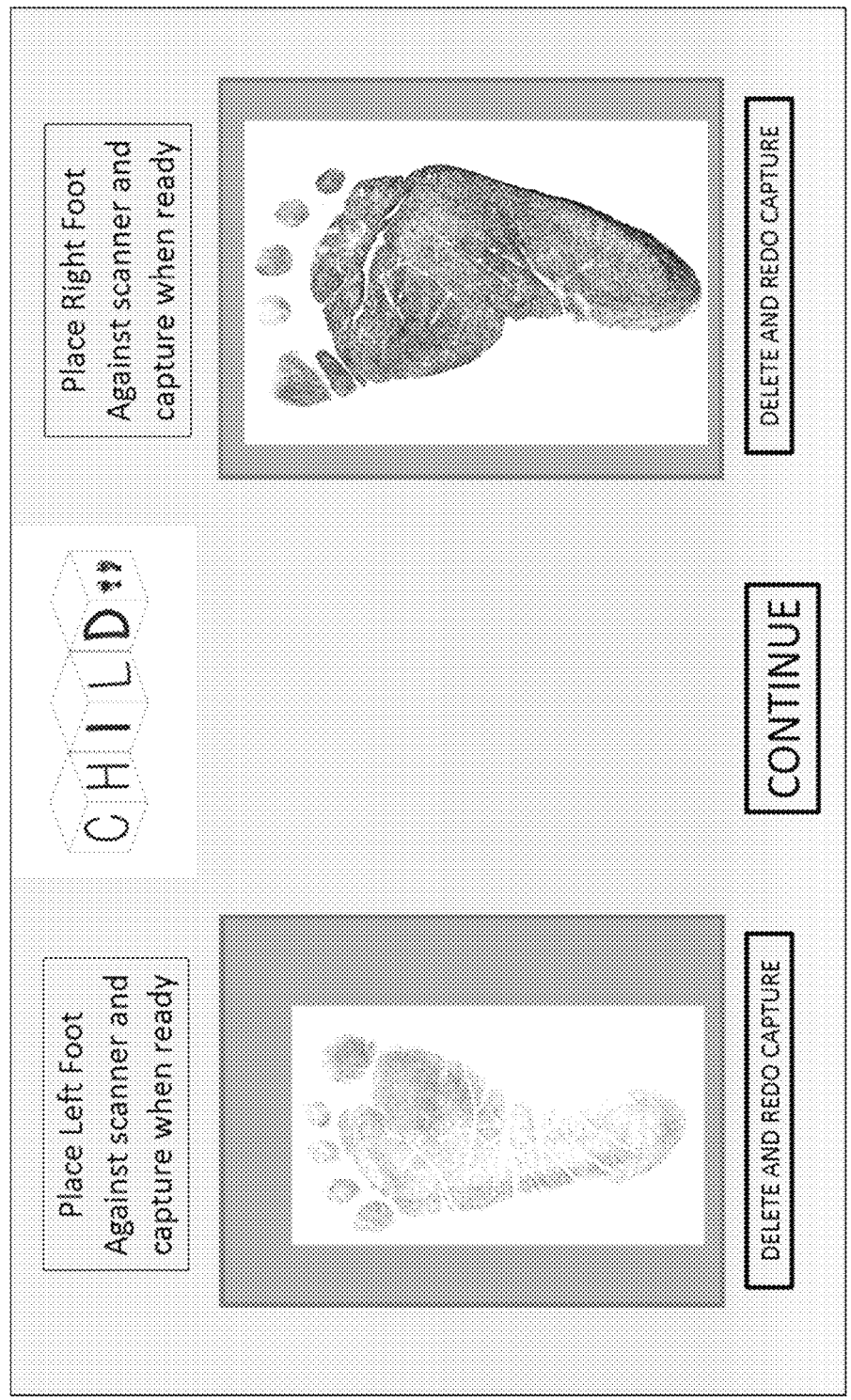
FIG. 4 illustrates some embodiments of the method of the present invention, showing two scanned/captured footprint images as inputs.

FIG. 4 shows a screenshot of an illustrative screen utilized to obtain footprint scan(s) in accordance with some embodiments of the instant invention.

Figure 5:
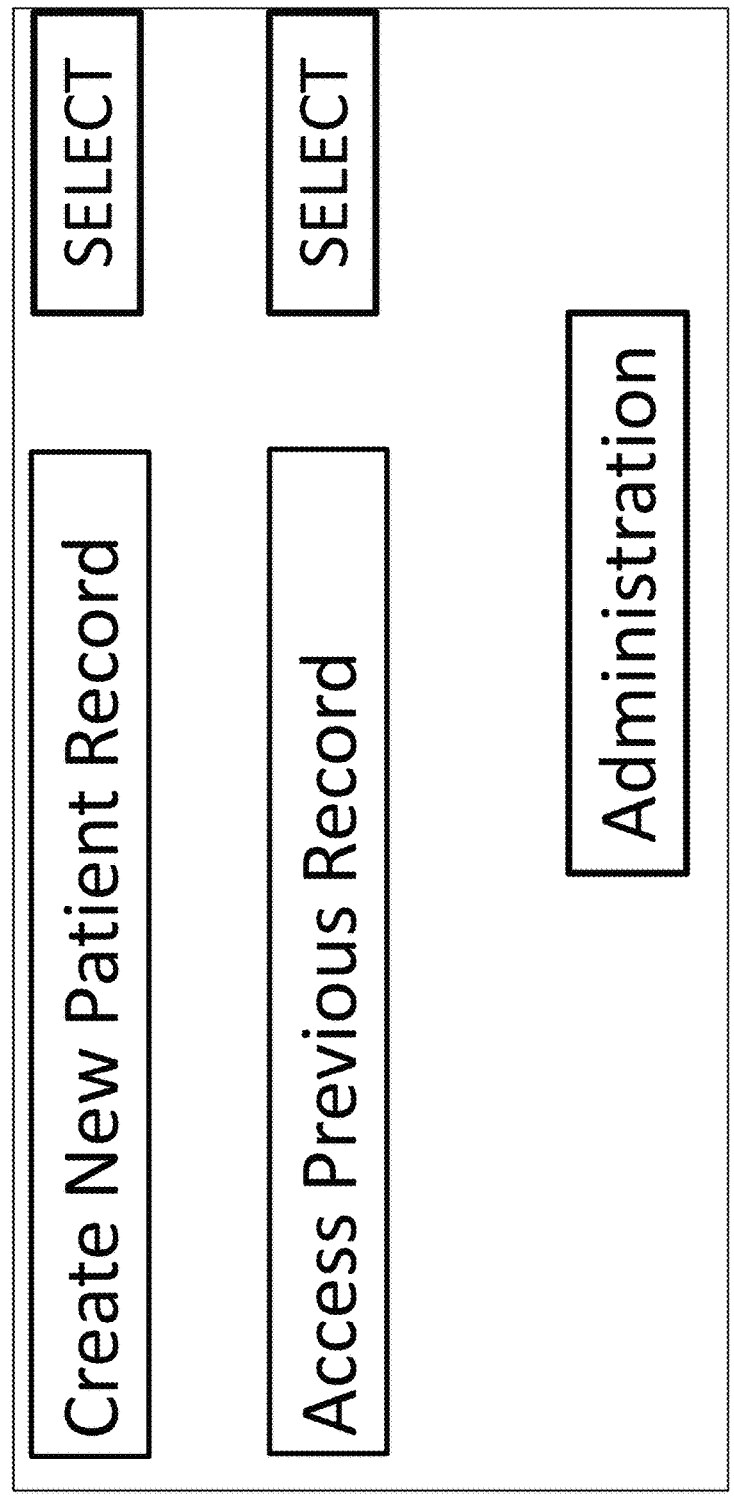
FIG. 5 illustrates some embodiments of the system of the present invention, showing selections available to a user.
Figure 8:
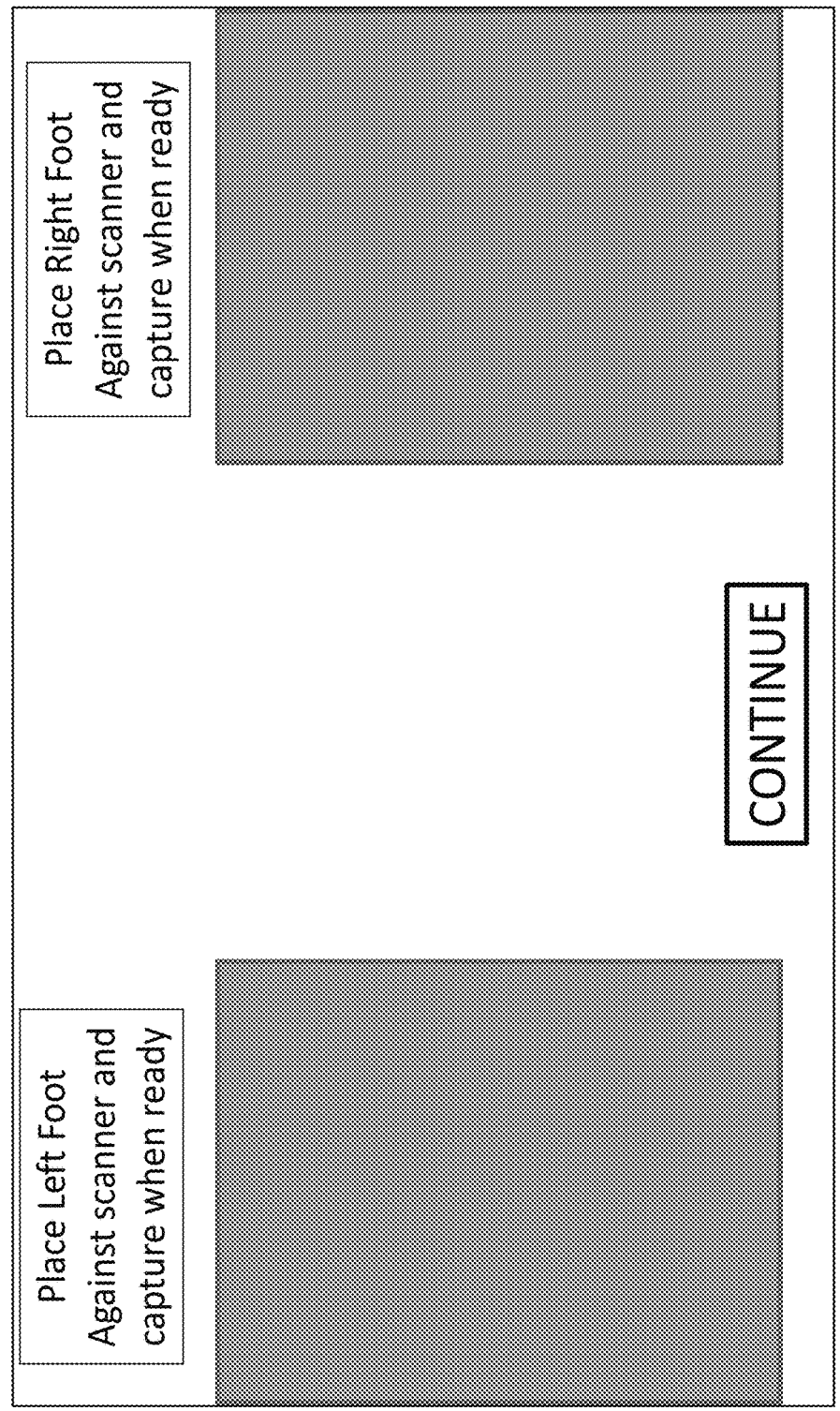
Figure 9:
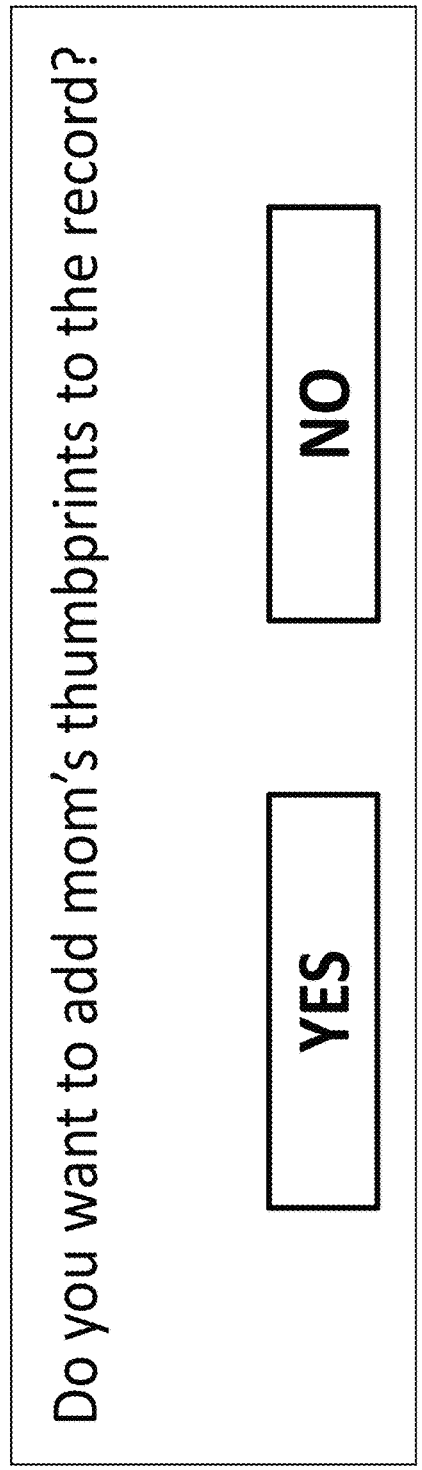
Figure 10:
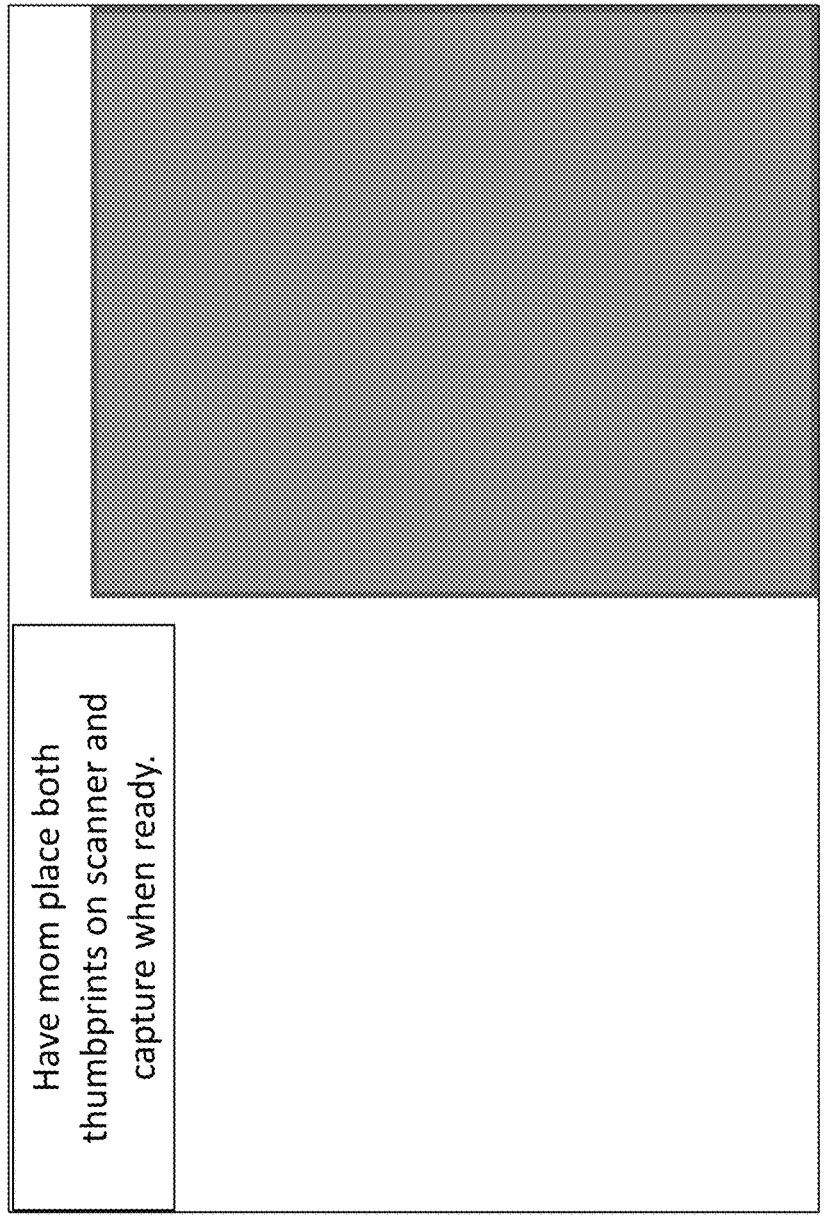
Figure 11:
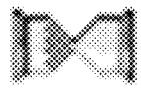
FIG. 11 illustrates some embodiments of the system of the present invention, showing the system correlating data.
Figure 12:
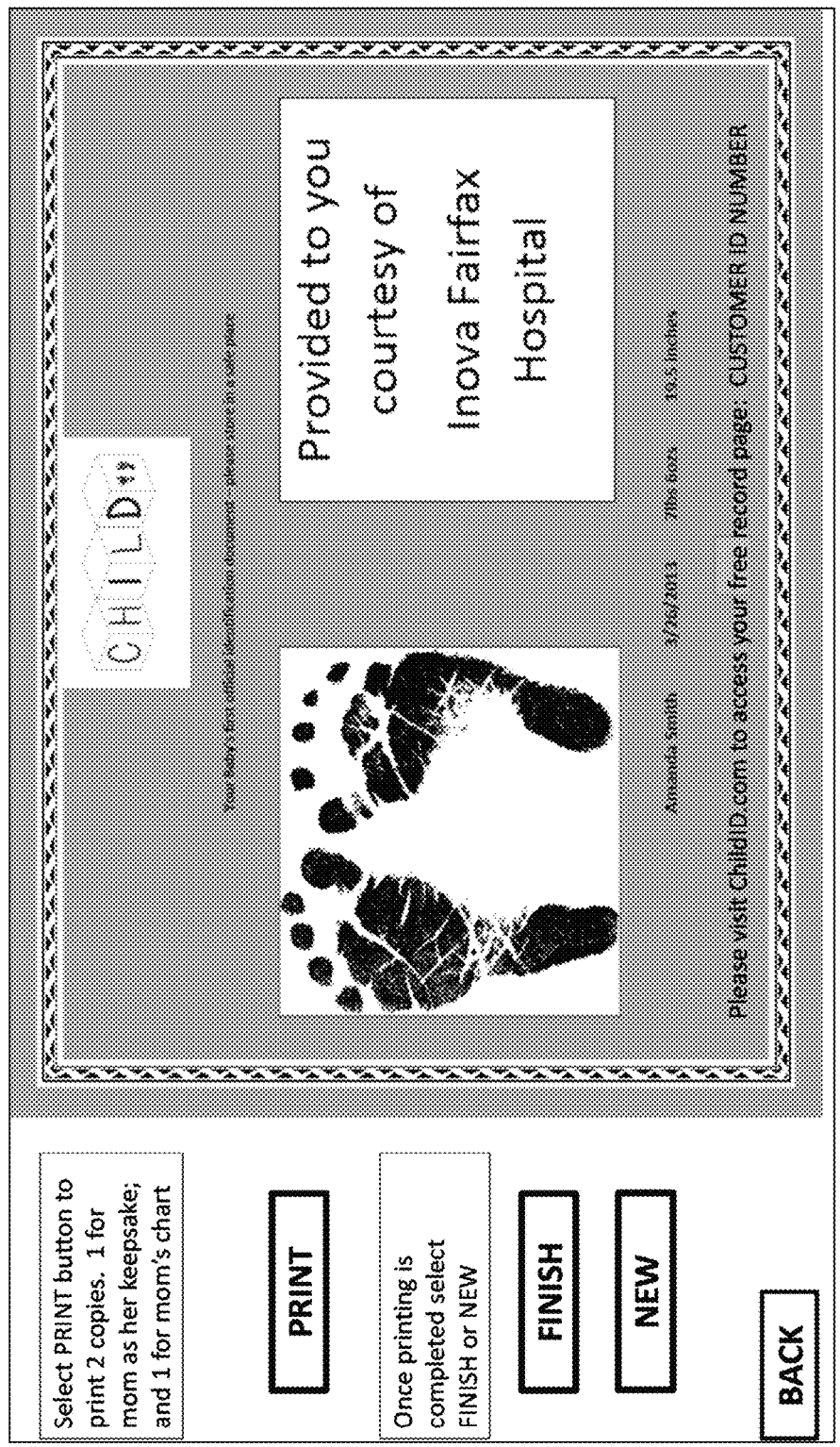
FIGS. 12-14 illustrate some embodiments of the system of the present invention, showing interfaces for providing a user to input selected data.
Figures 13, 14:
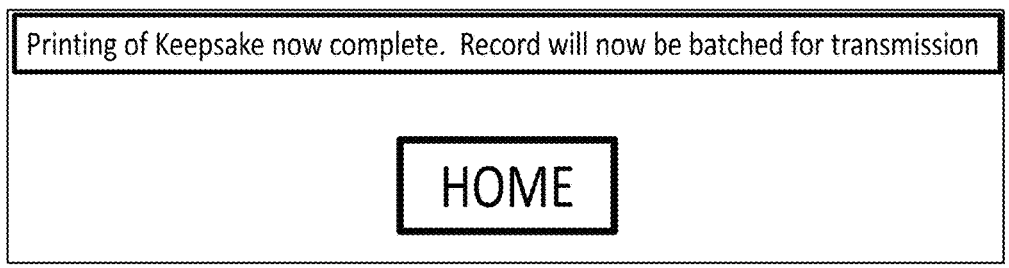
Figure 15:
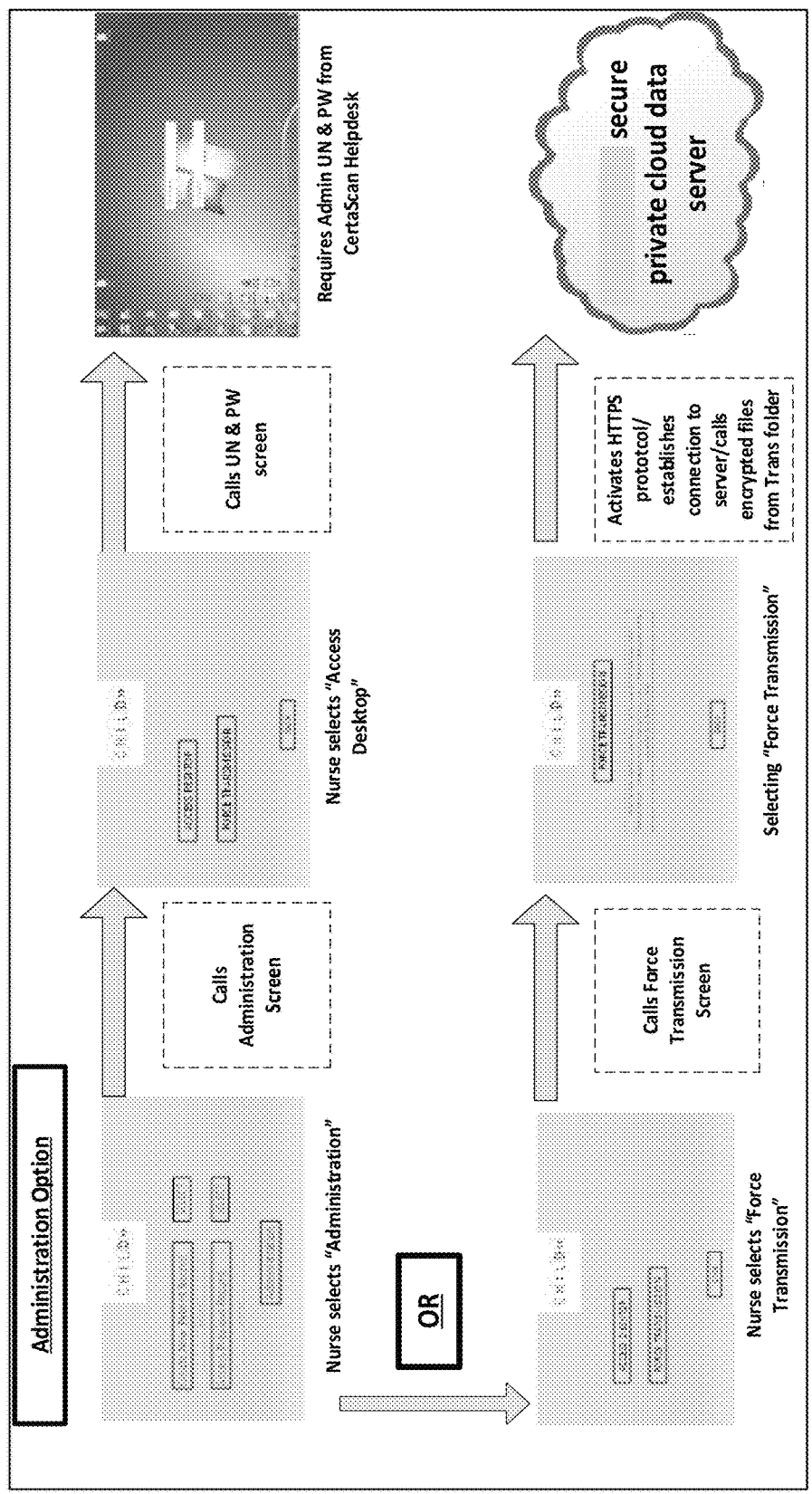
FIG. 15 illustrates some embodiments of the system of the present invention, showing a flow chart regarding the system responding to data input.
Figure 16:
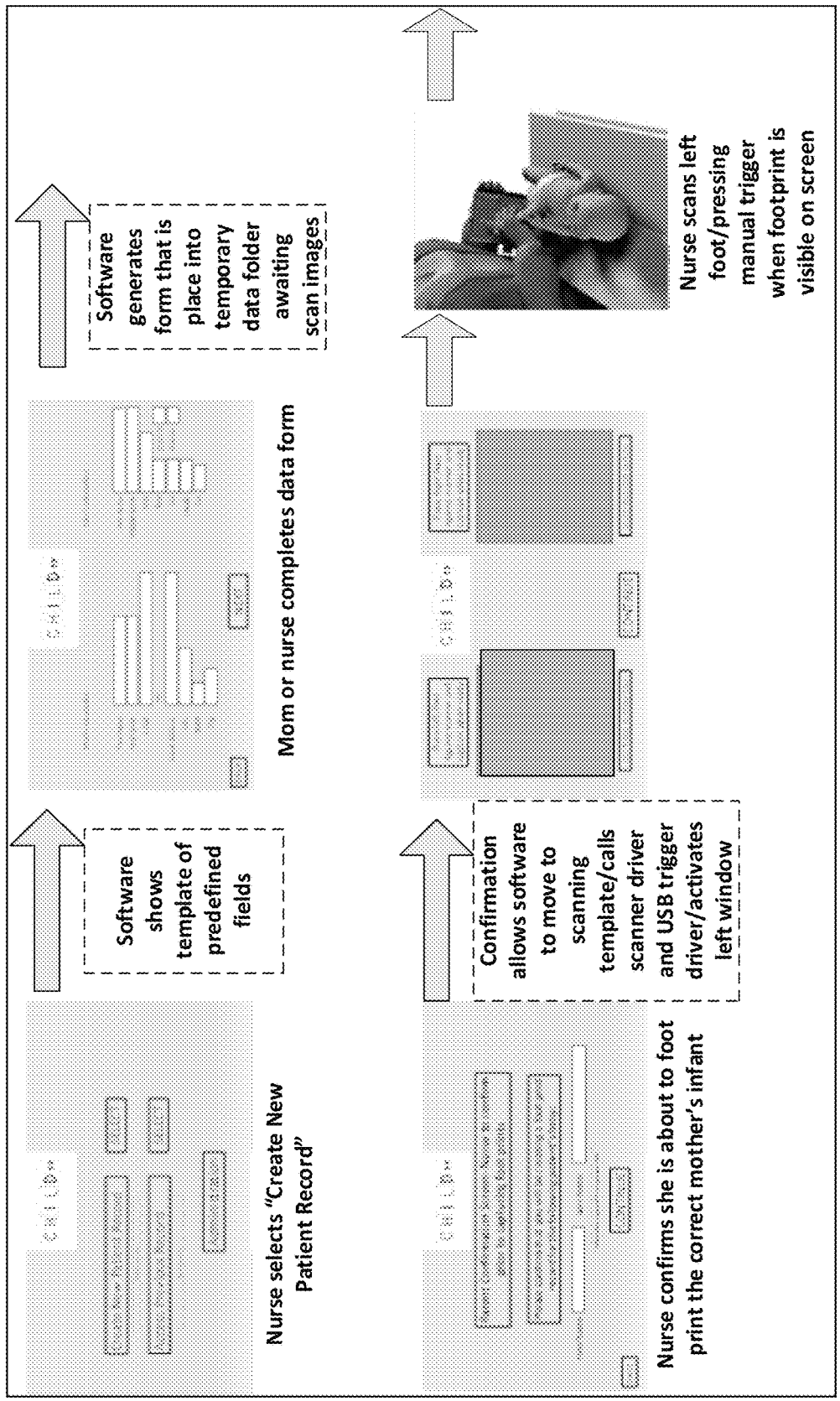
FIGS. 16-21 illustrate some embodiments of the system of the present invention, showing flow charts of the system.
Figure 17:
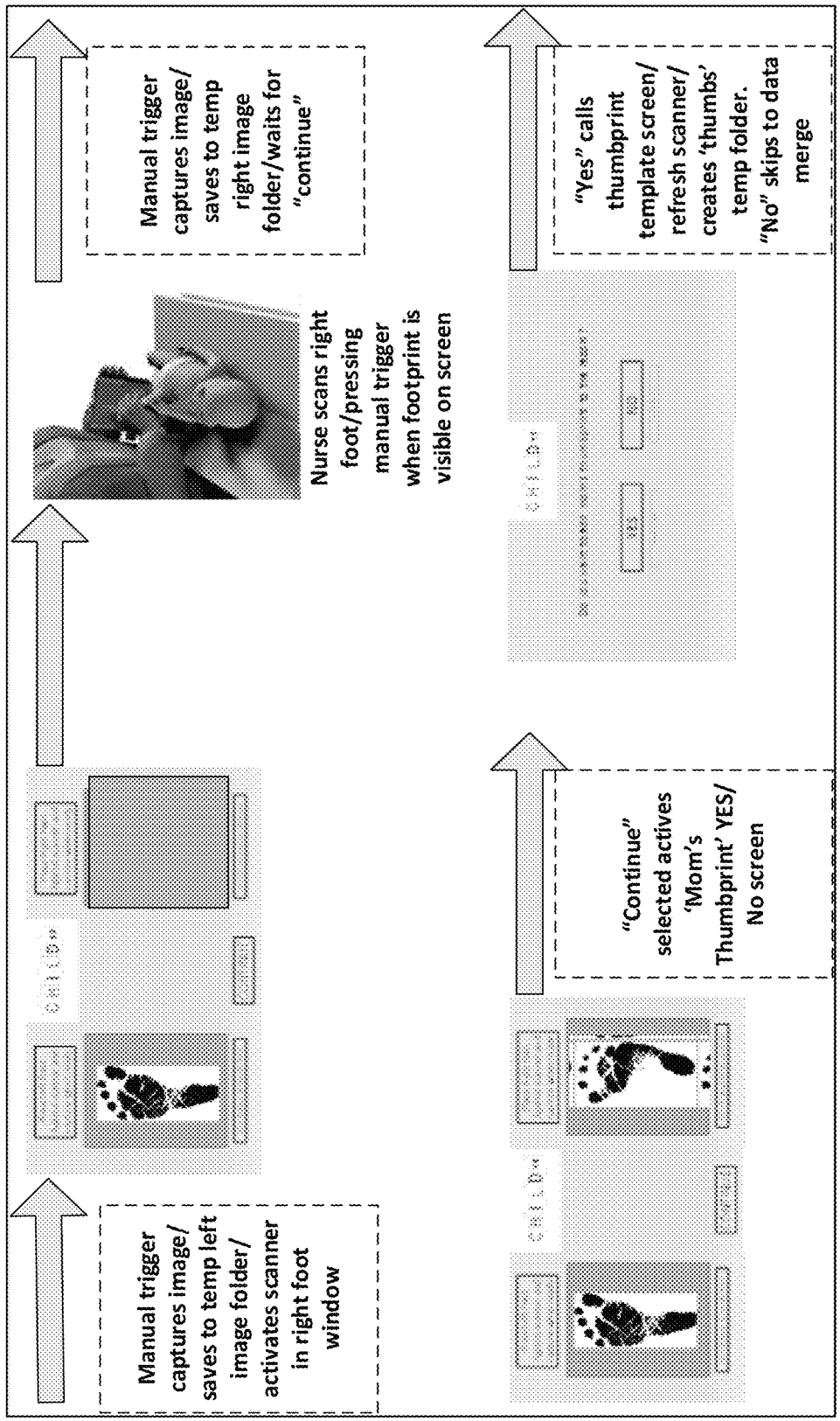
Figure 18:
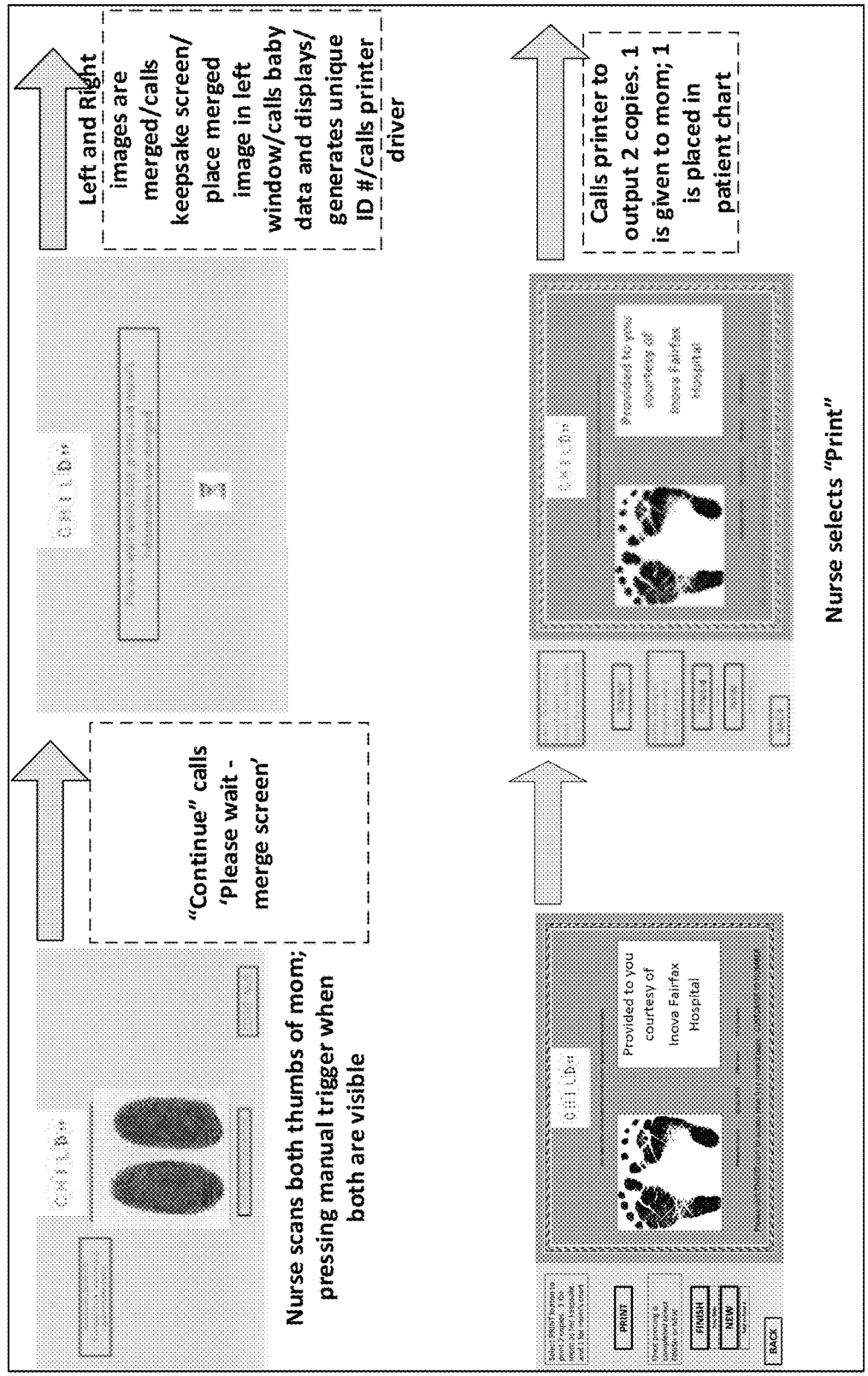
Figure 19:
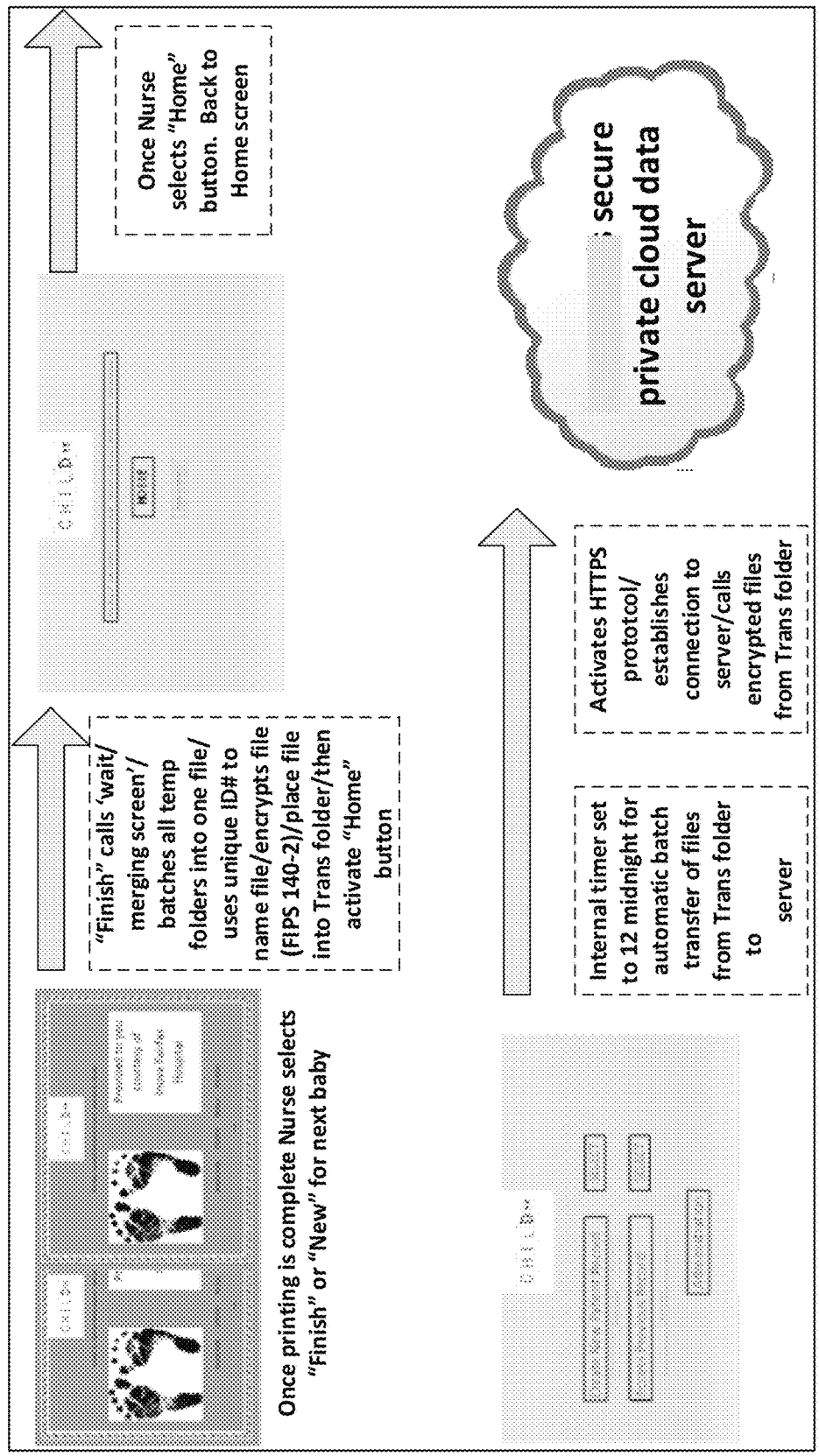
Figure 20:
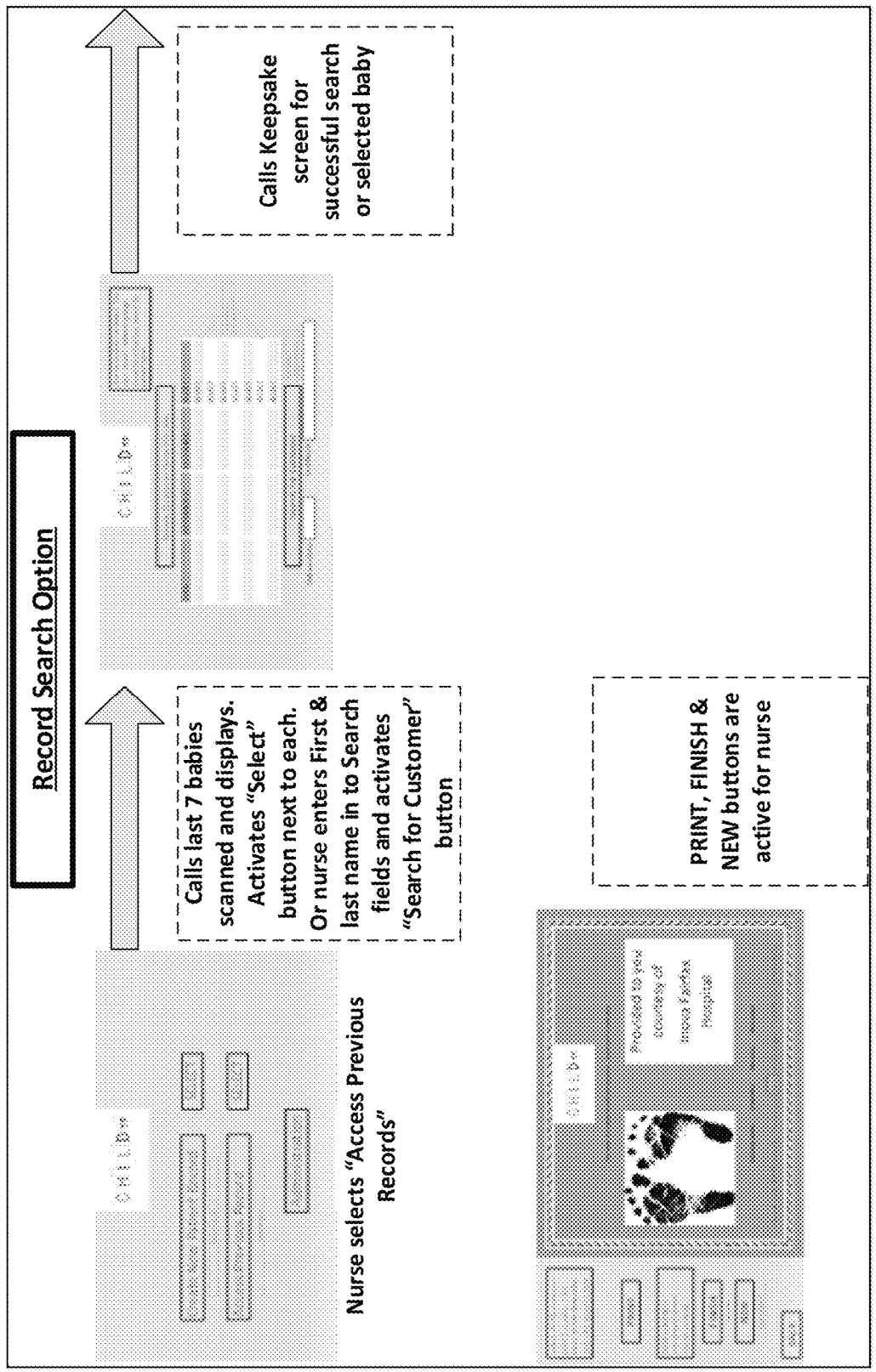
Figure 21:
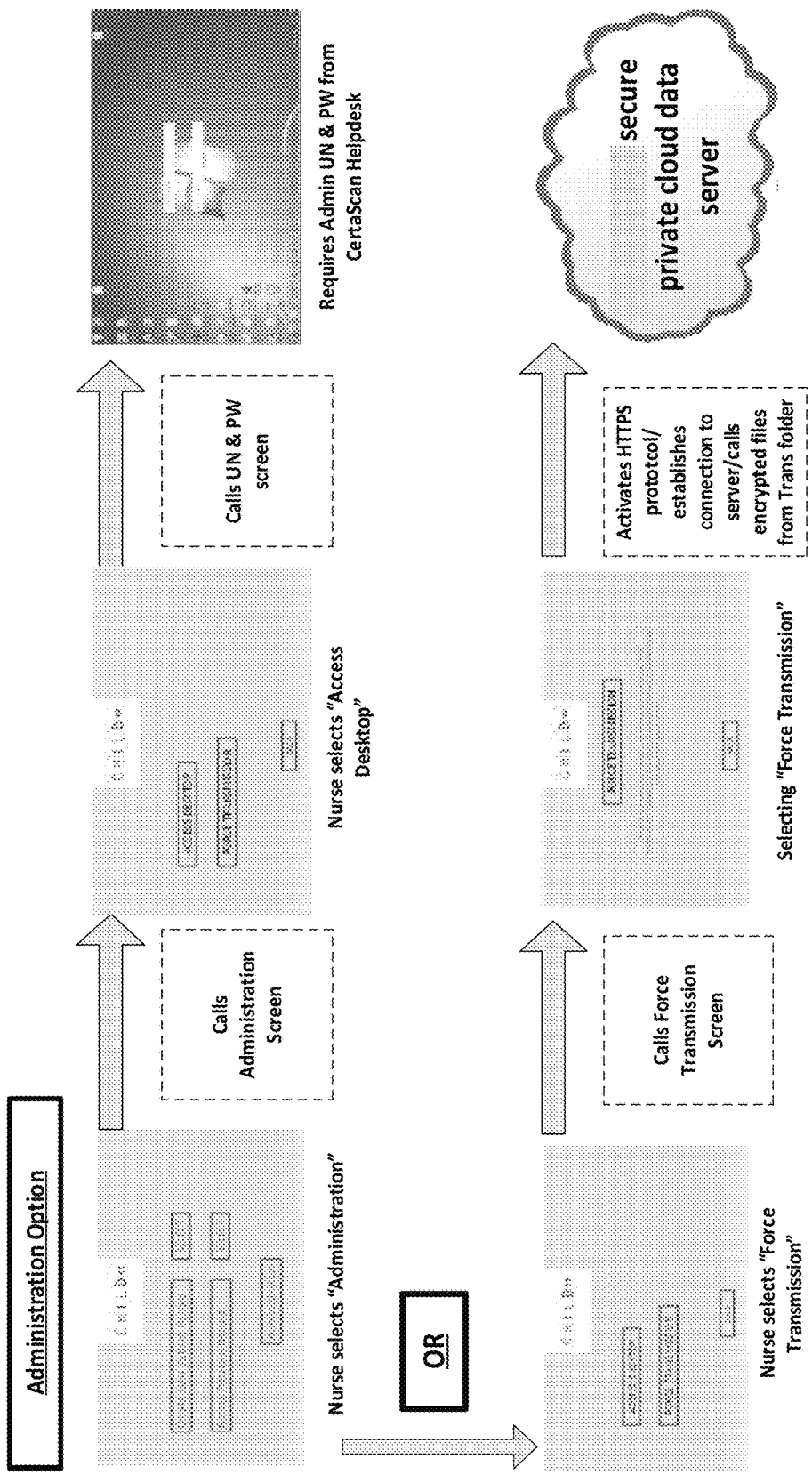

FIGS. 5-14 show screenshots of an illustrative process utilized to obtain, transmit, record, retrieve (historical tracking), and output newborn footprint scan(s) in accordance with some embodiments of the instant invention. In FIG. 5, clicking on a button "Create New Patient Record" advances a user to the screen of FIG. 6, and clicking on a button "Access Previous Record" advances the user to the screen of FIG. 14. In FIG. 7, the information is captured from the screen of FIG. 6. In FIG. 9, clicking on a button "Yes" advances a user to the screen of FIG. 10, and clicking on a button "No" advances the user to the screen of FIG. 11. In FIG. 12, clicking on a button "FINISH" advances a user to the screen of FIG. 13, and clicking on a button "NEW" returns the user to the screen of FIG. 5. In FIG. 14, clicking on button(s) "SELECT" generates the screen of FIG. 12, and clicking on a button "SEARCH FOR CUSTOMER" also generates the screen of FIG. 12.

Figure 26:
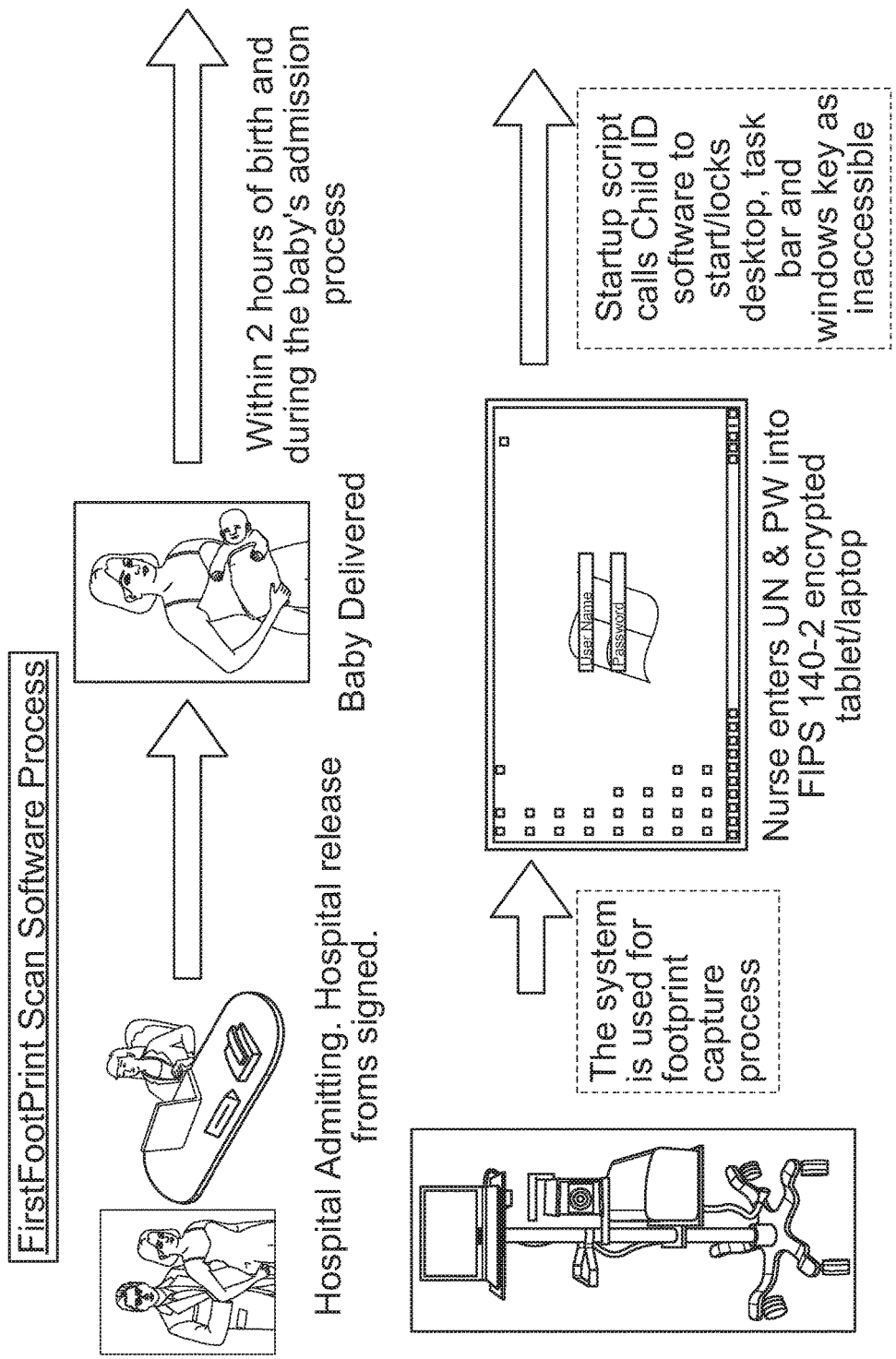
FIGS. 26-32 illustrate some embodiments of the system of the present invention, showing flow charts regarding the system.

FIG. 26 shows a screenshot of an illustrative flowchart in accordance with some embodiments of the instant invention.

Figure 27:
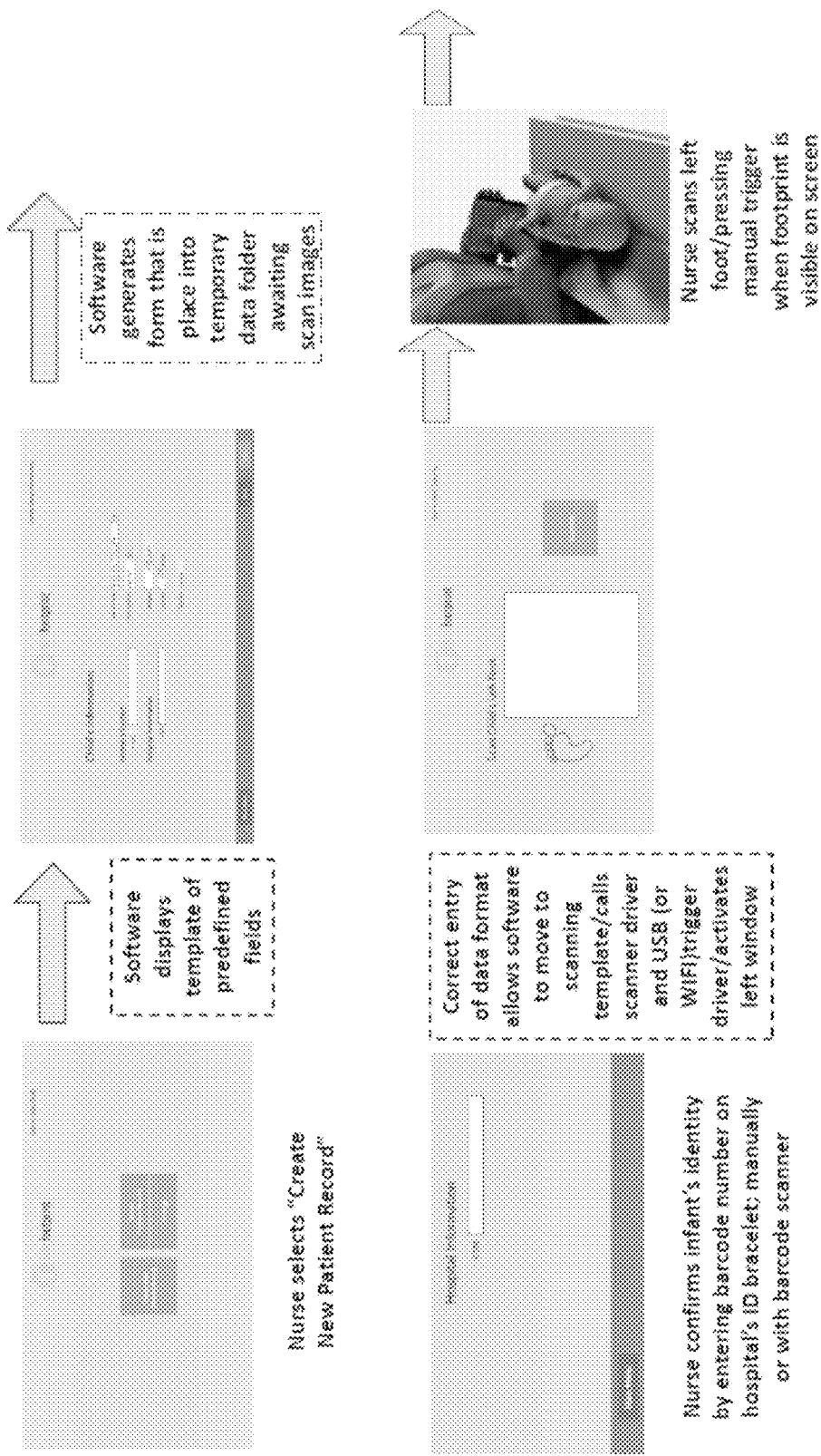

FIG. 27 shows a screenshot of an illustrative flowchart in accordance with some embodiments of the instant invention.

Figure 28:
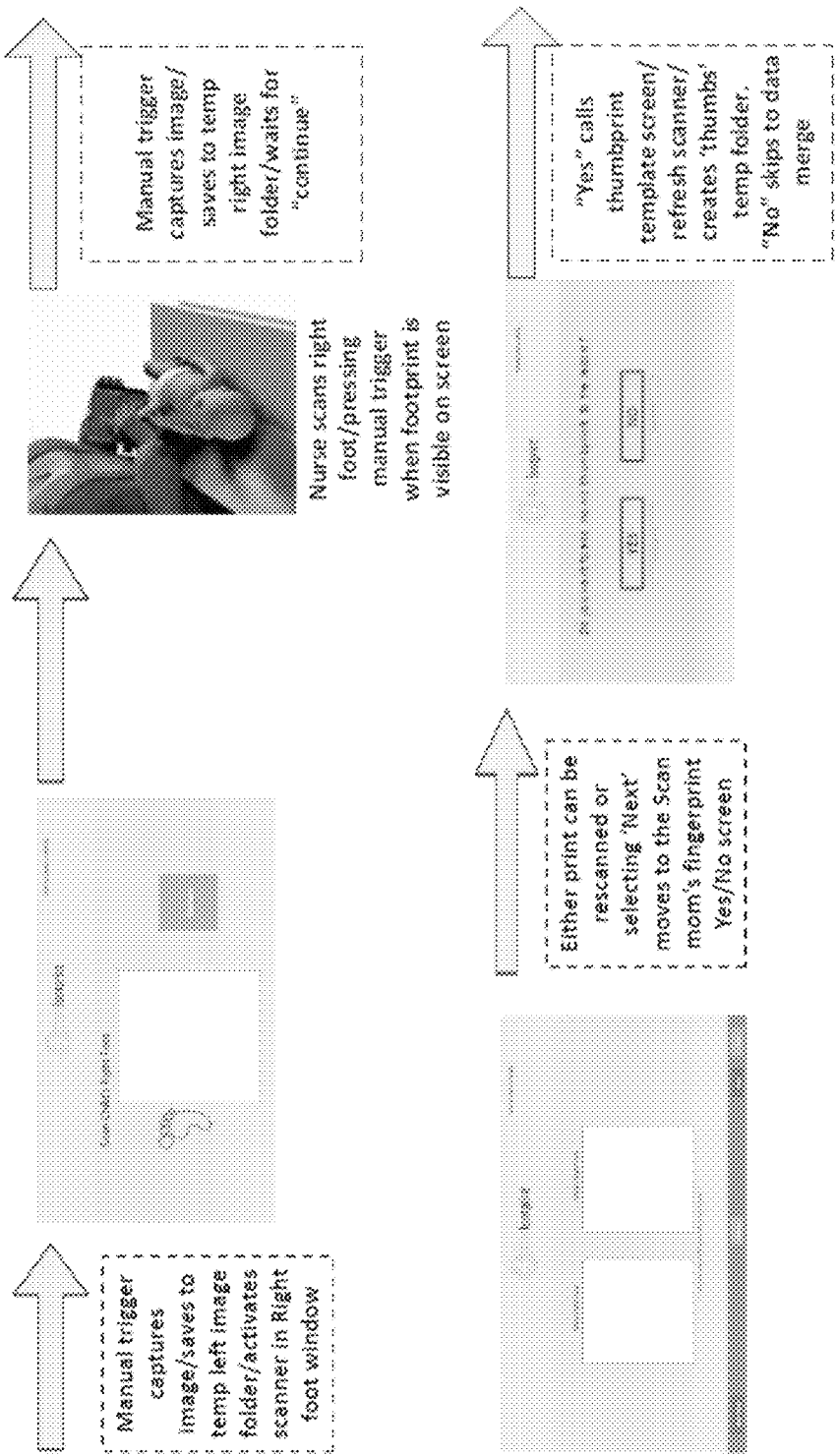

FIG. 28 shows a screenshot of an illustrative flowchart in accordance with some embodiments of the instant invention.

Figure 29:
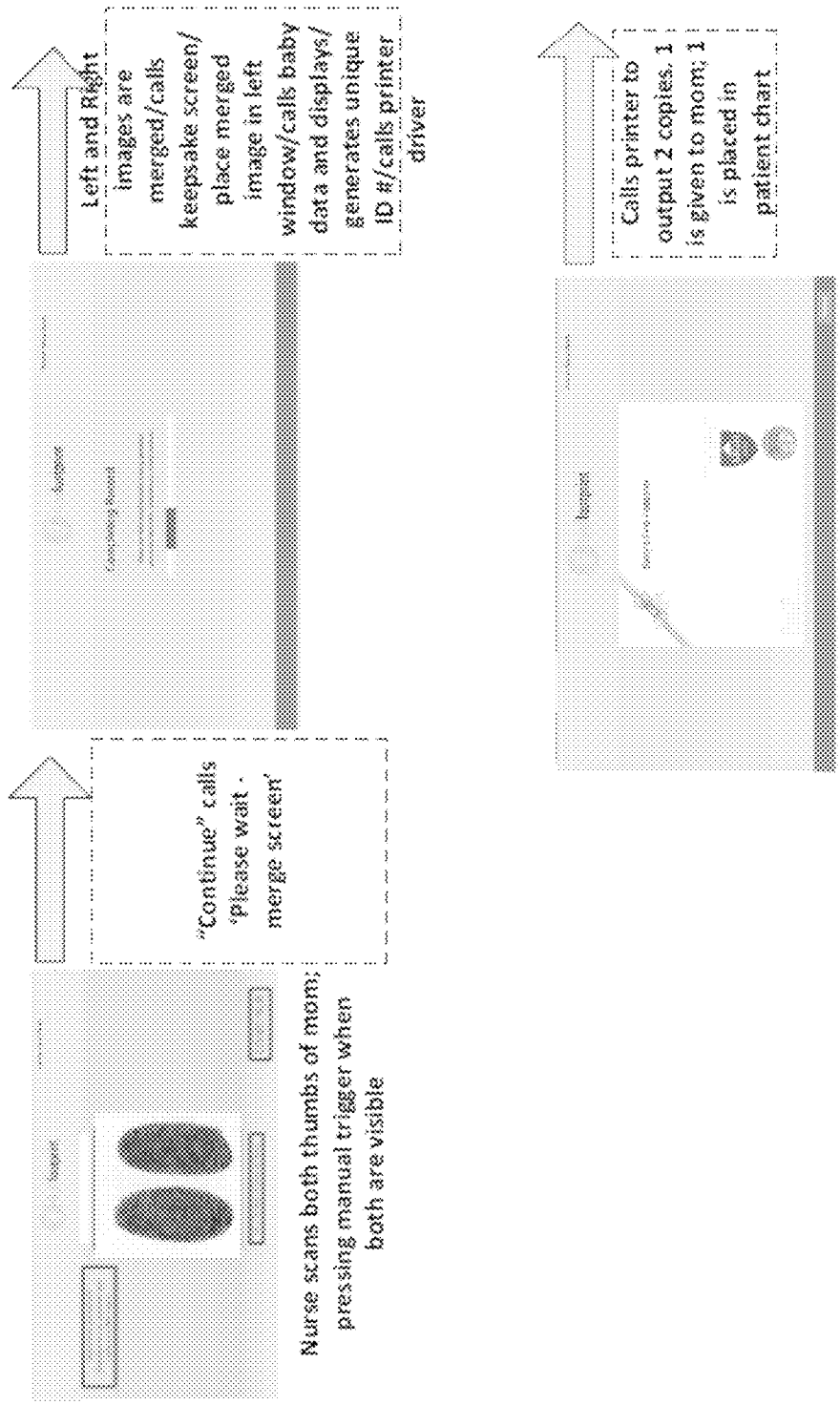

FIG. 29 shows a screenshot of an illustrative flowchart in accordance with some embodiments of the instant invention.

Figure 30:
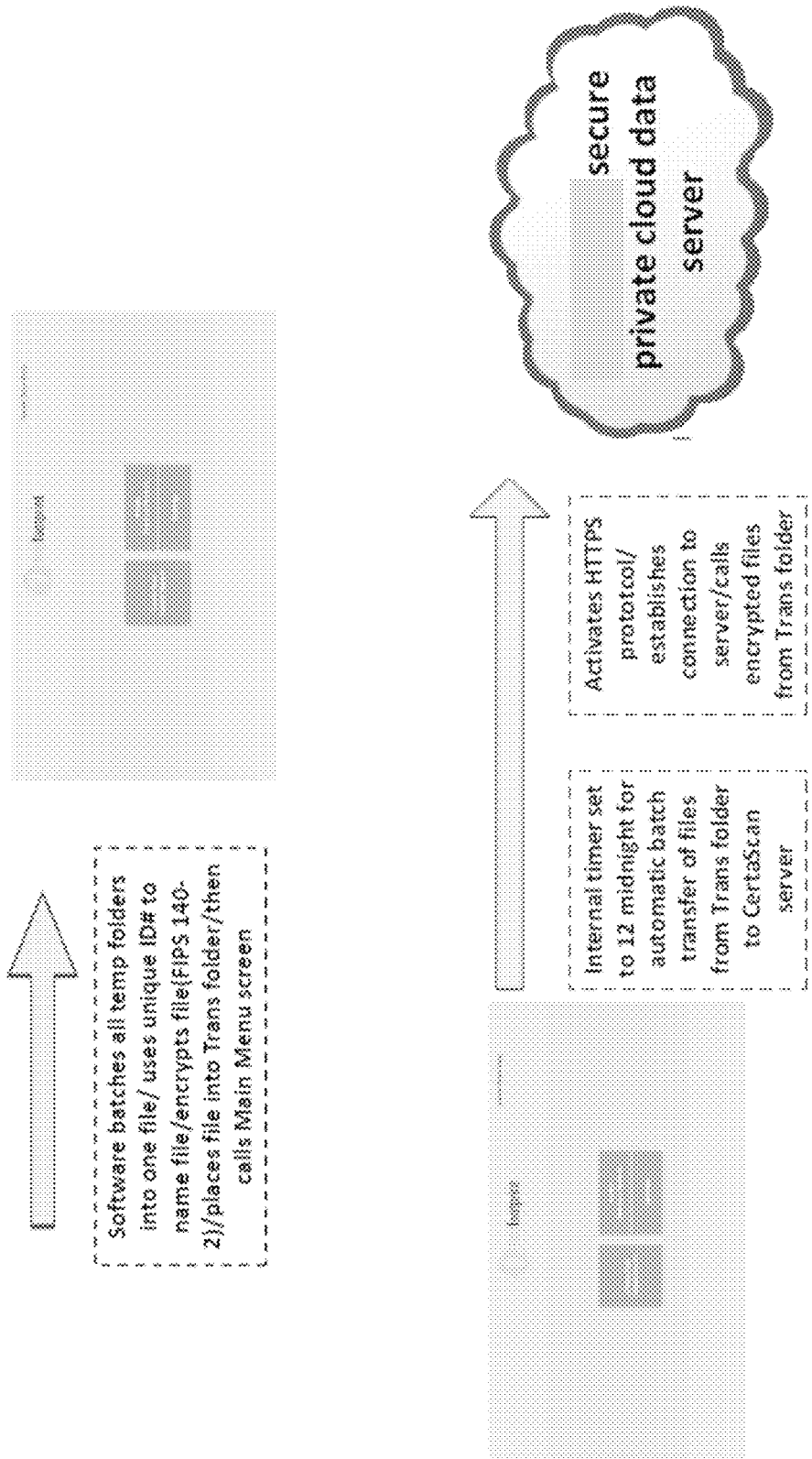

FIG. 30 shows a screenshot of an illustrative flowchart in accordance with some embodiments of the instant invention.

Figure 31:
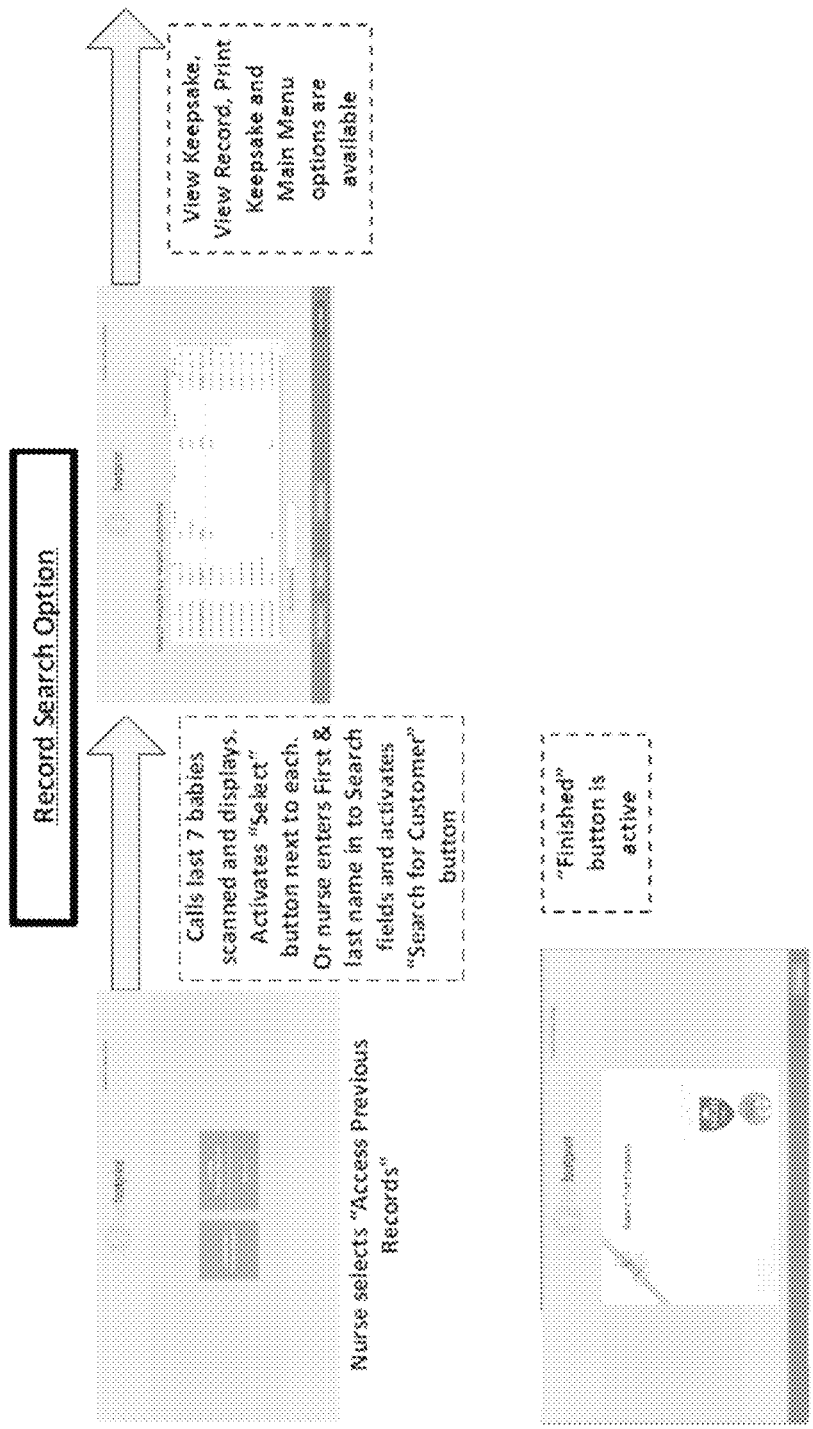

FIG. 31 shows a screenshot of an illustrative flowchart in accordance with some embodiments of the instant invention.

Figure 32:
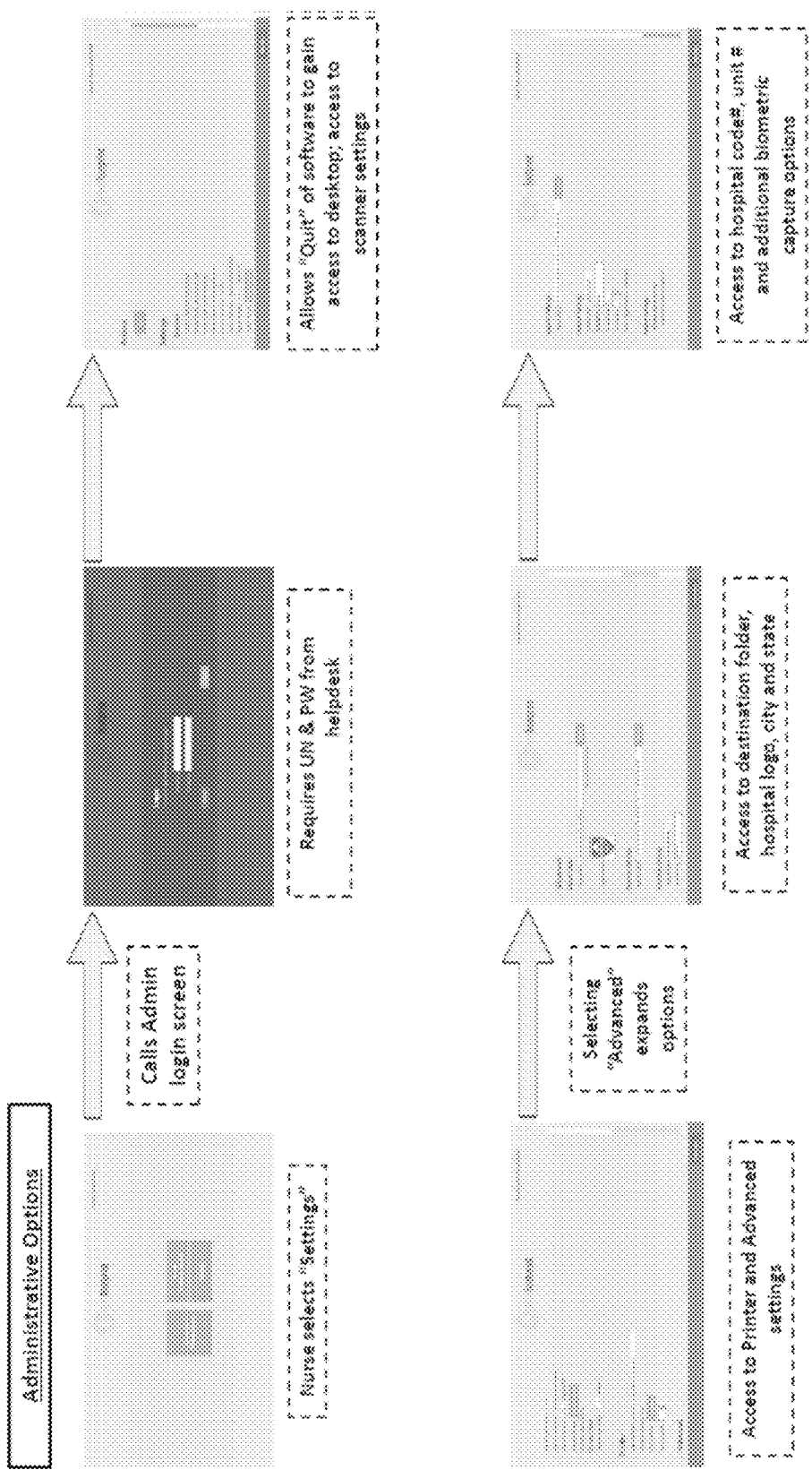

FIG. 32 shows a screenshot of an illustrative flowchart in accordance with some embodiments of the instant invention.

Figure 33:
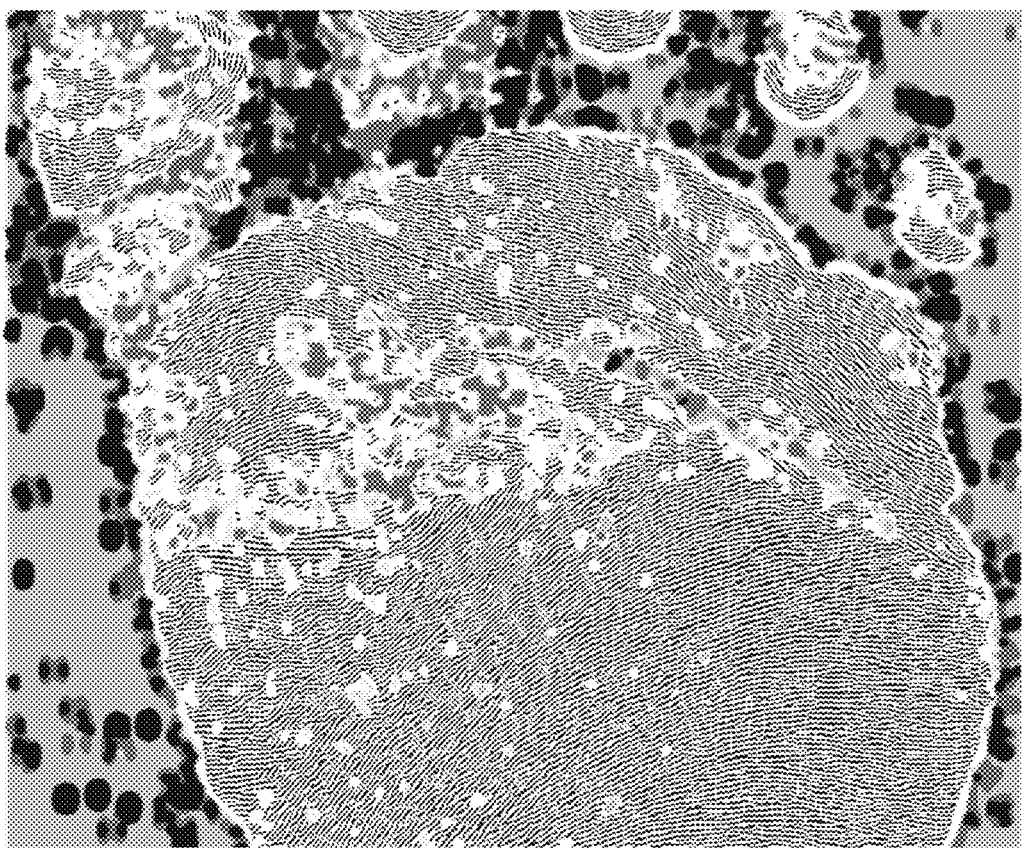
FIG. 33 illustrates an embodiment of the system of the present invention, showing a footprint obtained by the specialized scanner of the system.
Figure 34A:
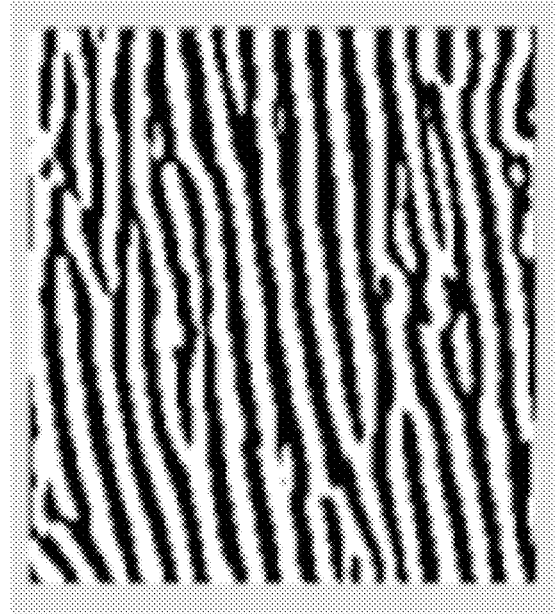
FIGS. 34A and 34B illustrate embodiments of the system of the present invention, showing an extracted image of a footprint obtained by the specialized scanner of the system (FIG. 34A) and a high contrast ridge obtained from the extracted image of the footprint obtained by the specialized scanner of the system (FIG. 34B).
Figure 34B:
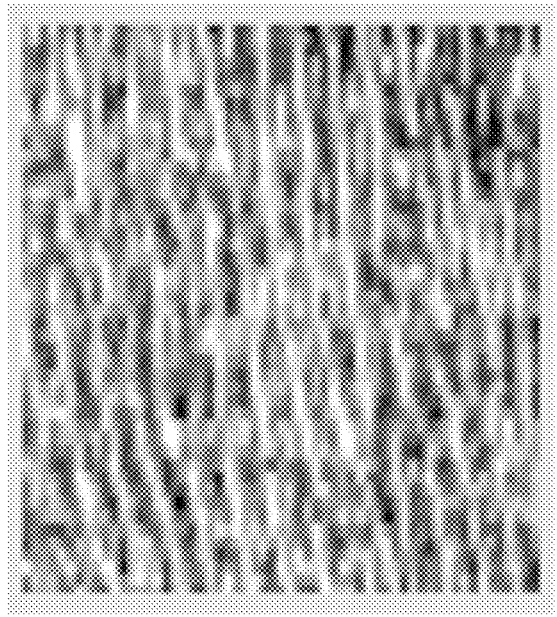

FIG. 33 shows a screenshot of an upper region of a footprint scan obtained in accordance with some embodiments of the instant invention.

FIG. 34A shows a screenshot of an illustrative image of an original extracted image and FIG. 34B shows a screenshot of an illustrative image obtained by extraction of ridges from a footprint (e.g., FIG. 34A) in accordance with some embodiments of the instant invention.

Figure 35:
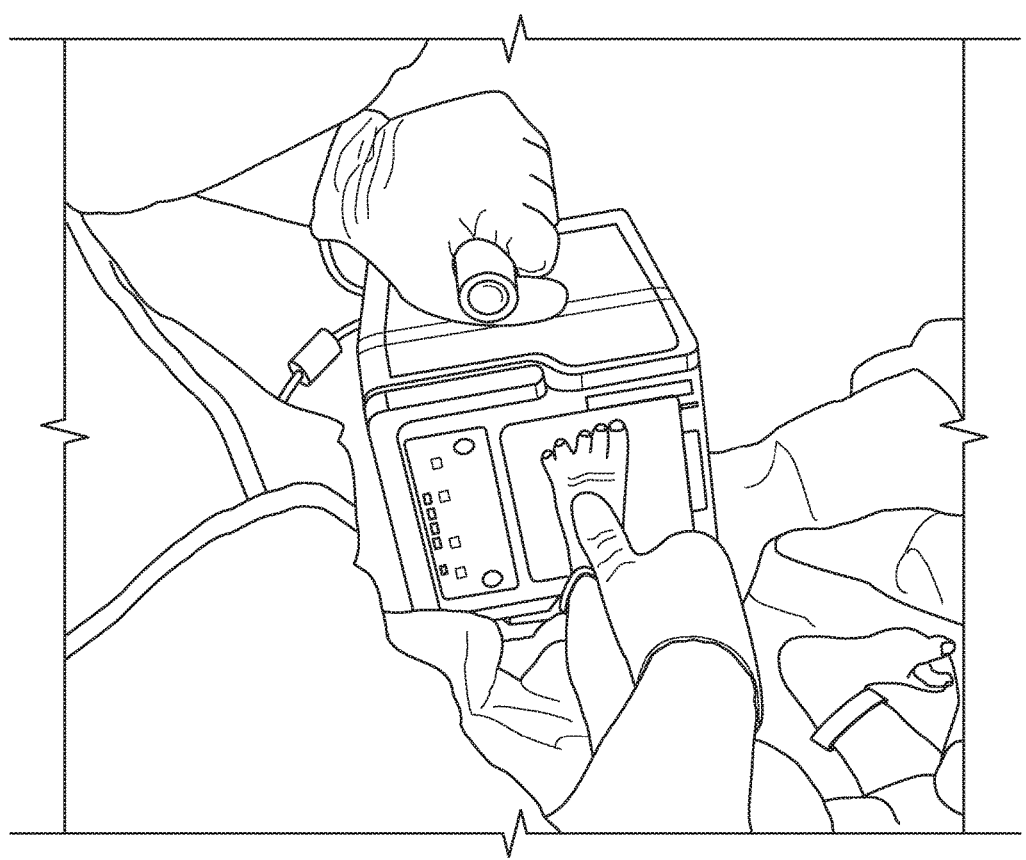
FIG. 35 illustrates an embodiment of the system of the present invention, showing a specialized scanner generating an image of a newborn baby's footprint.

FIG. 35 shows a photograph depicting a footprint scan obtained in accordance with some embodiments of the instant invention.

Figure 36:
FIG. 36 illustrates an embodiment of the system of the present invention, showing a printout generated by the system.

FIG. 36 shows an embodiment of a footprint scan obtained in accordance with some embodiments of the instant invention.

FIGS. 15-21 and FIGS. 26-32 show screenshots of illustrative processes utilized to obtain, transmit, record, process, retrieve (historical tracking), and output newborn footprint scan(s) in accordance with some embodiments of the instant invention. As FIGS. 15-21 show, the screens of FIGS. 5-14 can be utilized in the data flow(s) of FIGS. 15-21 and FIGS. 26-32, but the data flow(s) of FIGS. 15-21 and FIGS. 26-32 are not limited to the implementations of FIGS. 5-14 and other suitable implementations would be apparent.

In some embodiments, the specifically programmed foot printing systems of the instant invention can be utilized for, but not limited to:

confirming person's (e.g., child's) identity for doctor's offices, hospital discharge/admission, border control, etc.;

administering of vaccinations;

administering of correct stored breast milk in NICU's;

providing an "Amber Alert" type phone app (e.g., in conjunction with NCMEC) that allows parents to instantly communicate with law enforcement and/or NCMEC of a missing child and transmit footprints, photo and/or description, and etc.

In some embodiments, the specifically programmed foot printing systems of the instant invention can function in accordance with a suitable uniform standard for generating and storing digital footprints similar to the AFIS system for fingerprints.

Illustrative Operating Environments

In some embodiments, the innovative programmed systems can be operated over other operating systems, such as, but not limited to, iOS and Android. In some embodiments, the innovative programmed systems can be native to a software platform and/or incorporate programing modules based at least in part on HTML5-based tools like PhoneGap or Sencha.

Figure 22:
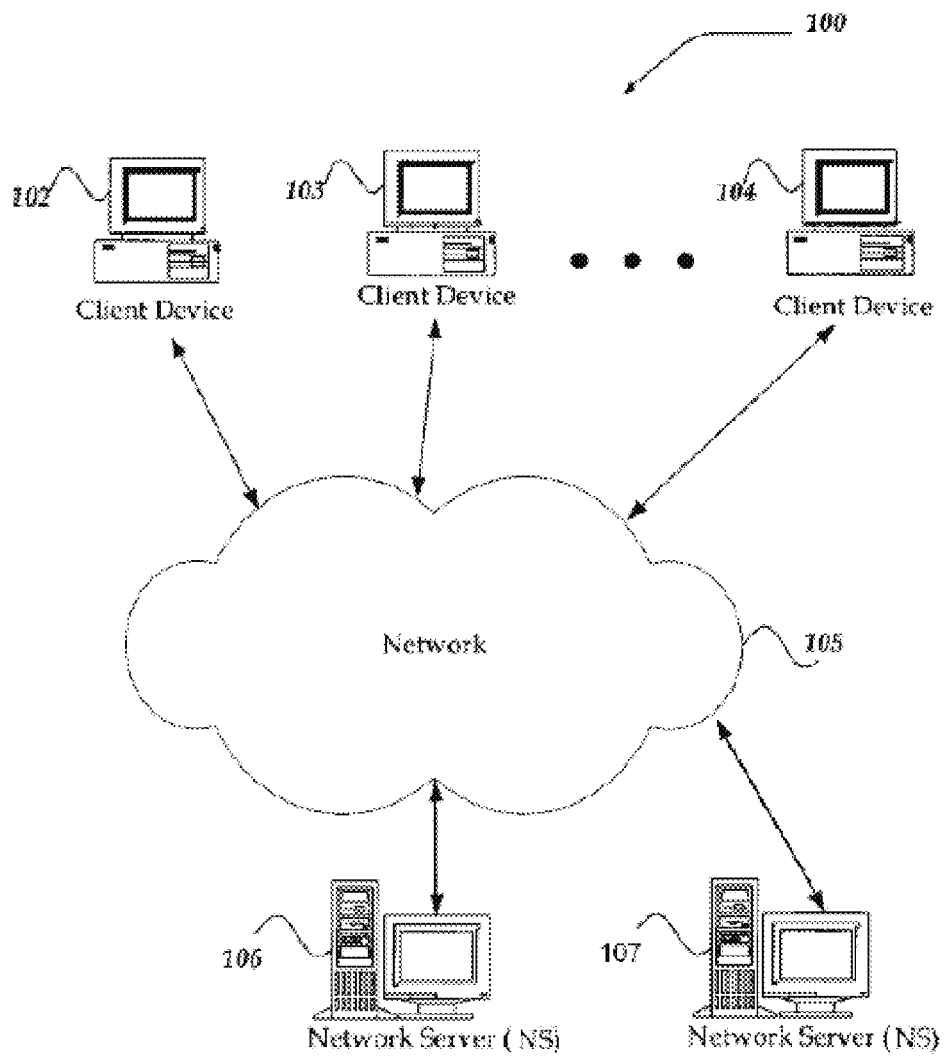
FIG. 22 illustrates some embodiments of the system of the present invention, showing network servers communicating with client devices by use of a network.

FIG. 22 illustrates one embodiment of an environment in which the present invention may operate. However, not all of these components may be required to practice the invention, and variations in the arrangement and type of the components may be made without departing from the spirit or scope of the invention. In some embodiment, the specifically programmed foot printing systems of the instant invention can host a large number (e.g., at least 10, at least 50, at least 100, at least 500, at least 1,000, at least 10,000; at least 100,000; at least 1,000,000) of members/participants (e.g., hospitals, healthcare professionals, police stations, policemen, etc.) and/or process a large number (e.g., at least 1,000; at least 10,000; at least 100,000; at least 1,000,000) of concurrent transactions (e.g., scan submissions, scan retrievals, scan recordings, scan comparisons, etc.). In other embodiments, the specifically programmed foot printing systems of the instant invention are based on a scalable computer and network architecture that incorporates varies strategies for assessing the data, caching, searching, and database connection pooling. An example of the scalable architecture is an architecture that is capable of operating multiple servers.

In embodiments, members of the inventive computer system 102-104 (e.g. user (e.g. players, agents, etc.) include virtually any computing device capable of receiving and sending a message over a network, such as network 105, to and from another computing device, such as servers 106 and 107, each other, and the like. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in some embodiments, client devices 102-104 are any device that is capable of connecting using a wired or wireless communication medium such as a PDA, POCKET PC, wearable computer, and any other device that is equipped to communicate over a wired and/or wireless communication medium.

In some embodiments, each member device within member devices 102-104 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, JavaScript, and the like. In embodiments, the invention is programmed in either Java or .Net.

In some embodiments, member devices 102-104 may be further configured to receive a message from the another computing device employing another mechanism, including, but not limited to email, Short Message Service (SMS), Multimedia Message Service (MMS), instant messaging (IM), internet relay chat (IRC), mIRC, Jabber, and the like.

In some embodiments, network 105 may be configured to couple one computing device to another computing device to enable them to communicate. In some embodiments, network 105 may be enabled to employ any form of computer readable media for communicating information from one electronic device to another. Also, in some embodiments, network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 105 includes any communication method by which information may travel between client devices 102-104, and servers 106 and 107.

Figure 23:
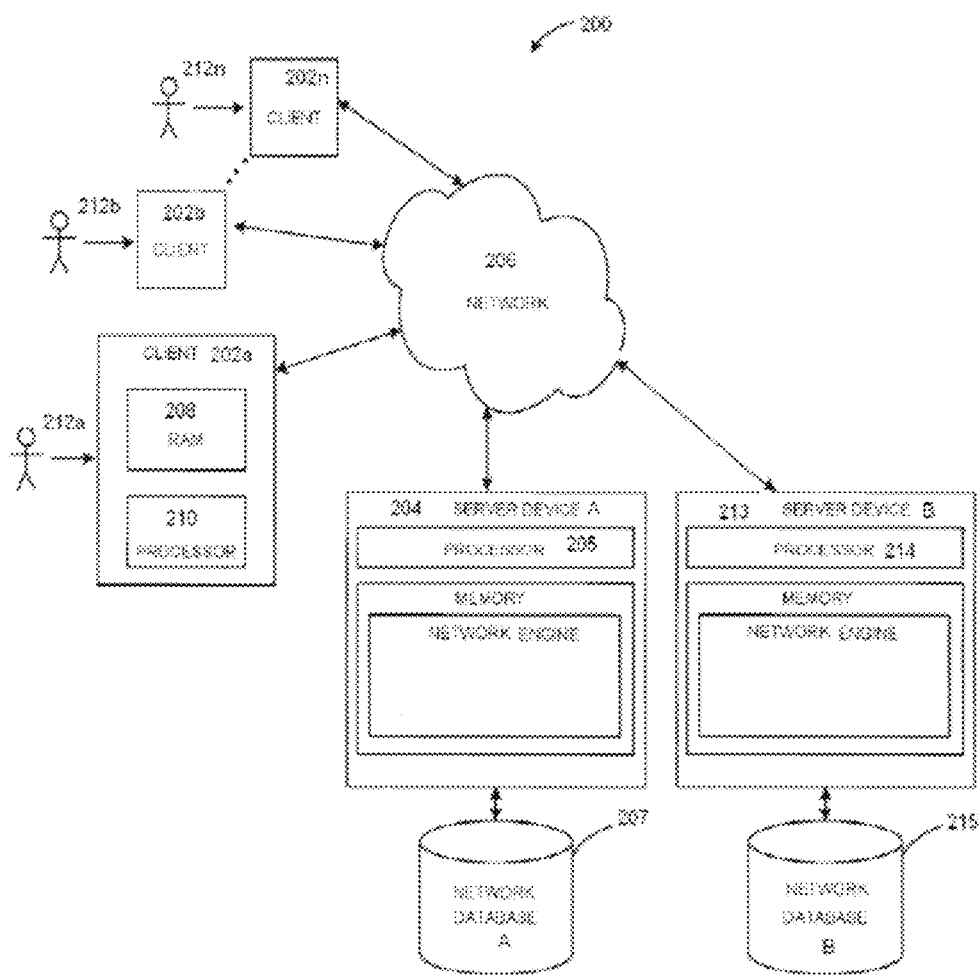
FIG. 23 illustrates some embodiments of the system of the present invention, showing a computer and network architecture that supports the inventive system.

FIG. 23 shows another exemplary embodiment of the computer and network architecture that supports the specifically programmed foot printing systems of the instant invention. The member devices 202a, 202b thru 202n shown (e.g., electronic scan devices, computers, portable devices, smartphones, etc.), each at least includes a computer-readable medium, such as a random access memory (RAM) 208 coupled to a processor 210 or FLASH memory. The processor 210 may execute computer-executable program instructions stored in memory 208. Such processors comprise a microprocessor, an ASIC, and state machines. Such processors comprise, or may be in communication with, media, for example computer-readable media, which stores instructions that, when executed by the processor, cause the processor to perform the steps described herein. In some embodiments of computer-readable media may include, but are not limited to, an electronic, optical, magnetic, or other storage or transmission device capable of providing a processor, such as the processor 210 of client 202a, with computer-readable instructions. Other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Member devices 202a-n may also comprise a number of external or internal devices such as a mouse, a CD-ROM, DVD, a keyboard, a display, or other input or output devices. Examples of client devices 202a-n may be personal computers, digital assistants, personal digital assistants, cellular phones, mobile phones, smart phones, pagers, digital tablets, laptop computers, Internet appliances, and other processor-based devices. In general, a client device 202a can be any type of processor-based platform that is connected to a network 206 and that interacts with one or more application programs. Client devices 202a-n may operate on any operating system capable of supporting a browser or browser-enabled application, such as Microsoft™, Windows™, or Linux. The client devices 202a-n shown may include, for example, personal computers executing a browser application such as Microsoft Corporation's Internet Explorer™, Apple Computer, Inc.'s Safari™, Mozilla Firefox, and Opera. Through the client devices 202a-n, users (e.g. players, agents, etc.) 212a-n communicate over the network 206 with each other and with other systems and devices coupled to the network 206. As shown in FIG. 23, server devices 204 and 213 may be also coupled to the network 206.

Figure 24:
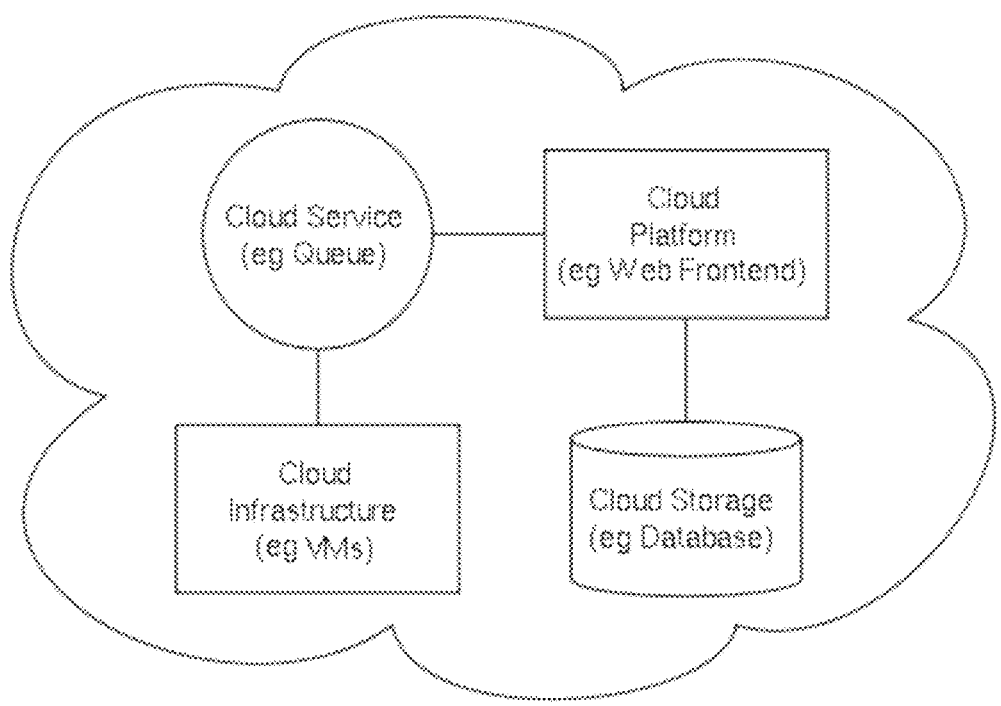
FIG. 24 illustrates some embodiments of the system of the present invention, showing a cloud system supporting the inventive system.
Figure 25:
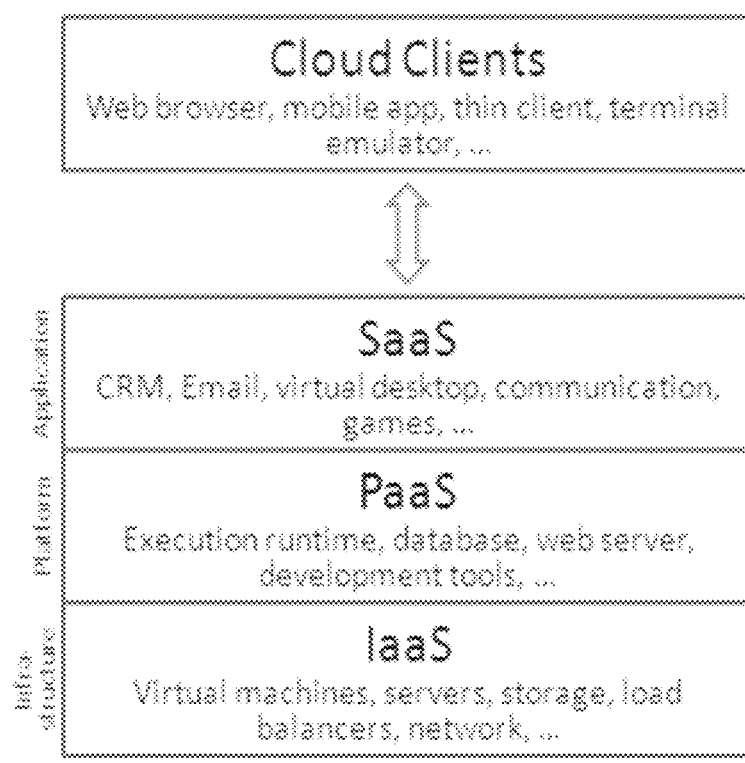
FIG. 25 illustrates some embodiments of the system of the present invention, showing the cloud systems supporting the inventive system and allowing a delivering and receiving of information to and/or from cloud clients.

For purposes of the instant description, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). In some embodiments, the instant invention offers/manages the cloud computing/architecture as, but not limiting to: infrastructure a service (IaaS), platform as a service (PaaS), and software as a service (SaaS). FIGS. 24 and 25 illustrate schematics of exemplary implementations of the cloud computing/architecture.

In some embodiments, the term "mobile electronic device" may refer to any portable electronic device that may or may not be enabled with location tracking functionality. For example, a mobile electronic device can include, but is not limited to, a mobile phone, tablet, Personal Digital Assistant (PDA), Blackberry™, Pager, Smartphone, or any other reasonable mobile electronic device. For ease, at times the above variations are not listed or are only partially listed, this is in no way meant to be a limitation.

In some embodiments, the instant invention utilizes location tracking technology or locating method to identify a location of, for example, a scanner. In some embodiments, the instant invention utilizes Radio Frequency Identification such as, but not limited to, any form of RFID tag for automatic tracking and/or automatic importing/accessing/retrieving of data.

In some embodiments, the instant invention can utilize near-field wireless communication (NFC) (e.g., for communicating with scanners) that can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiments, this can enable NFC targets to take very simple form factors such as tags, stickers, key fobs, or cards that do not require batteries. In some embodiments, NFC peer-to-peer communication can be conducted when a plurality of NFC-enable devices are within close proximity of each other.

In some embodiments, the instant invention provides for a computer system, including: 1) a specialized scanner designed to capture: i) a plurality of forensic quality images of at least one foot print of an infant within a second, and ii) at least one forensic quality image of at least one finger print of a mother, where the forensic quality images have a forensic quality that is achieved when: at least 80% of the plurality of forensic quality images have a gray-scale dynamic range of at least 200 gray-levels, and at least 99% of the plurality of forensic quality images have a dynamic range of at least 128 gray-levels; 2) at least one server having software stored in a computer readable medium accessible by the at least one server; where the software is at least configured to: i) receive, in real-time: a) the plurality of the forensic quality images of the at least one foot print of the infant captured by the specialized scanner, b) the at least one forensic quality image of the at least one finger print of the mother captured by the specialized scanner; and c) at least one identification parameter of the mother; ii) generate, in real-time, at least one customer identification number and correlate, in real-time, the at least one customer identification number with: a) the plurality of forensic quality image of the at least one foot print of the infant captured by the specialized scanner, b) the at least one forensic quality image of the at least one finger print of the mother captured by the specialized scanner; and c) the input of the at least one identification parameter of the mother; iii) select, in real-time, at least one sharpest forensic quality image of the at least one foot print of the infant from the plurality of forensic quality image of the at least one foot print of the infant captured by the specialized scanner; iv) store, in real-time, in at least one database accessible by the at least one server, in real-time: a) the at least one sharpest forensic quality image of the at least one foot print of the infant captured by the specialized scanner, b) the at least one forensic quality image of the at least one finger print of the mother captured by the specialized scanner, and c) the at least one identification parameter of the mother and the at least one customer identification number; iv) create, in real-time, a correlation, in the at least one database, between the at least one sharpest forensic quality image of the at least one foot print of the infant and the at least one forensic quality image of the at least one finger print of the mother; v) generate at least one output based, at least in part, on the correlation between the at least one sharpest forensic quality image of the at least one foot print of the infant and the at least one forensic quality image of the at least one finger print of the mother; and 3) a plurality of specifically programmed input/output devices, where each specifically programmed input device is configured to: i) receive, in real-time, for each infant having at least one respective sharpest forensic quality image stored in the at least one database, at least one command input wherein the at least one command input has at least one of: at least one particular identification parameter and the at least one particular customer identification number; ii) retrieve, in real-time, at least one particular sharpest forensic quality image of the at least one foot print of the infant from the at least one database; and iii) display, in real-time, the at least one particular sharpest forensic quality image of the at least one foot print of the infant; where the at least one server, the at least one database and the plurality of specifically programmed input devices communicate through a computer network.

In some embodiments, the system further includes a specifically programmed printer configured to produce hardcopy images, where the hardcopy images maintain sharpness and detail rendition structure up to at least 4× magnification.

In some embodiments, the system is configured to electronically compare at least one first forensic quality image of at least one first foot print of the infant captured by the specialized scanner at a first time point with at least one second forensic quality image of at the least one second foot print of the infant captured by the specialized scanner captured at a second time point to determine the at least one sharpest forensic quality image of the at least one foot print of the infant.

In some embodiments, the system is further configured to: for each forensic quality image of the at least one foot print of the infant, extract, in real-time, ridge detail within a predetermined area of such forensic quality image, creating, in real-time, at least one topographic representation of such forensic quality image based, at least in part, on ridge detail; and matching, in real-time, the at least one topographic representation of such forensic quality image of the at least one foot print of the infant to at least one other topographic representation of at least one other image of at least one other foot print of at least one other infant.

In some embodiments, the at least one identification parameter includes: at least one email address of the mother, at least one cell phone number of the mother, at least one home phone number of the mother, at least one address of the mother, at least one password provided by the mother, or any combination thereof.

In some embodiments, the output is at least one of: at least one printout, at least one graphical image shown on a graphical user interface of at least one specifically programmed input/output device, and any combination thereof. In some embodiments, the at least one printout is a keepsake personalized with information related to a facility in which the infant has been delivered. In some embodiments, the software is further configured to: encrypt and decrypt, in real-time, communications between the at least one server, the at least one database and the plurality of specifically programmed input devices. In some embodiments, the plurality of specifically programmed input devices are at least a thousand of specifically programmed input devices; and where the at least one server is configured to manage, in real-time, the at least a thousand of specifically programmed input devices.

In some embodiments, the instant invention provides for a computer method, including: 1) capturing by use of a specialized scanner: i) a plurality of forensic quality images of at least one foot print of an infant within a second, and ii) at least one forensic quality image of at least one finger print of a mother, where the forensic quality images have a forensic quality that is achieved when: at least 80% of the plurality of forensic quality images have a gray-scale dynamic range of at least 200 gray-levels, and at least 99% of the plurality of forensic quality images have a dynamic range of at least 128 gray-levels; 2) receiving, in real-time: a) the plurality of the forensic quality images of the at least one foot print of the infant captured by the specialized scanner, b) the at least one forensic quality image of the at least one finger print of the mother captured by the specialized scanner; and c) at least one identification parameter of the mother; 3) generating, in real-time, at least one customer identification number and correlating, in real-time, the at least one customer identification number with: a) the plurality of forensic quality image of the at least one foot print of the infant captured by the specialized scanner, b) the at least one forensic quality image of the at least one finger print of the mother captured by the specialized scanner; and c) the input of the at least one identification parameter of the mother; 4) selecting, in real-time, at least one sharpest forensic quality image of the at least one foot print of the infant from the plurality of forensic quality image of the at least one foot print of the infant captured by the specialized scanner; 5) storing, in real-time, in at least one database accessible by the at least one server, in real-time: a) the at least one sharpest forensic quality image of the at least one foot print of the infant captured by the specialized scanner, b) the at least one forensic quality image of the at least one finger print of the mother captured by the specialized scanner, and c) the at least one identification parameter of the mother and the at least one customer identification number; 6) creating, in real-time, a correlation, in the at least one database, between the at least one sharpest forensic quality image of the at least one foot print of the infant and the at least one forensic quality image of the at least one finger print of the mother; 7) generating at least one output based, at least in part, on the correlation between the at least one sharpest forensic quality image of the at least one foot print of the infant and the at least one forensic quality image of the at least one finger print of the mother; 8) receiving, by a plurality of specifically programmed input/output devices, in real-time, for each infant having at least one respective sharpest forensic quality image stored in the at least one database, at least one command input wherein the at least one command input has at least one of: at least one particular identification parameter and the at least one particular customer identification number; 9) retrieving, by a plurality of specifically programmed input/output devices, in real-time, at least one particular sharpest forensic quality image of the at least one foot print of the infant from the at least one database; and 10) displaying, by a plurality of specifically programmed input/output devices, in real-time, the at least one particular sharpest forensic quality image of the at least one foot print of the infant.

In some embodiments, the method further includes: producing hardcopy images by use of a specifically programmed printer, where the hardcopy images maintain sharpness and detail rendition structure up to at least 4× magnification. In some embodiments, the method further includes electronically comparing at least one first forensic quality image of at least one first foot print of the infant captured by the specialized scanner at a first time point with at least one second forensic quality image of at the least one second foot print of the infant captured by the specialized scanner captured at a second time point to determine the at least one sharpest forensic quality image of the at least one foot print of the infant.

In some embodiments, the method further includes: extracting, in real-time, for each forensic quality image of the at least one foot print of the infant, ridge detail within a predetermined area of such forensic quality image, creating, in real-time, at least one topographic representation of such forensic quality image based, at least in part, on ridge detail; and matching, in real-time, the at least one topographic representation of such forensic quality image of the at least one foot print of the infant to at least one other topographic representation of at least one other image of at least one other foot print of at least one other infant.

In some embodiments, the at least one identification parameter includes: at least one email address of the mother, at least one cell phone number of the mother, at least one home phone number of the mother, at least one address of the mother, at least one password provided by the mother, or any combination thereof. In some embodiments, the output is at least one of: at least one printout, at least one graphical image shown on a graphical user interface of at least one specifically programmed input/output device, and any combination thereof. In some embodiments, the at least one printout is a keepsake personalized with information related to a facility in which the infant has been delivered.

In some embodiments, the method further includes: encrypting and decrypting, in real-time, communications between the at least one server, the at least one database and the plurality of specifically programmed input devices.

In some embodiments, the plurality of specifically programmed input devices are at least a thousand of specifically programmed input devices; and where the at least one server is configured to manage, in real-time, the at least a thousand of specifically programmed input devices.

While a number of embodiments of the present invention have been described, it is understood that these embodiments are illustrative only, and not restrictive, and that many modifications may become apparent to those of ordinary skill in the art.

What is claimed is:

1. A computer system, comprising:
   1) a specialized forensic quality scanner designed to capture:
      i) a plurality of forensic quality foot prints of an infant at a birth time, and
      ii) at least one forensic quality finger print of a mother of the infant,
   wherein the specialized forensic quality scanner comprises:
      i) a scanning unit, and
      ii) a computer, storing first software and having a visual display;
   wherein, when executing the first software, the computer is configured to generate a graphical user interface having at least one designated area to display a foot print of the infant when a foot of the infant touches a scanning surface of the scanning unit before an operator of the specialized forensic quality scanner activates the scanning unit to capture the plurality of forensic quality foot prints of the infant based on a visual appearance of the foot print within the at least one designated area;

wherein the plurality of forensic quality foot prints of the infant has a forensic quality that is achieved when:

each respective foot print of the infant has an identifiable friction ridge minutiae, allowing to electronically differentiate the infant from another infant based on respective identifiable friction ridge minutiae, at least 80% of the forensic quality foot prints have a gray-scale dynamic range of at least 200 gray-levels, and at least 99% of the plurality of forensic quality foot prints have a dynamic range of at least 128 gray-levels;

2) at least one server having second software stored in a non-transitory computer readable medium;

wherein, when executing the second software, the at least one server is at least configured to:

receive, in real-time:
a) the plurality of the forensic quality foot prints of the infant,
b) the at least one forensic quality finger print of the mother, and
c) at least one identification parameter of the mother;

generate, in real-time, at least one customer identification number and associate, in real-time, the at least one customer identification number with:
a) the plurality of forensic quality foot prints of the infant,
b) the at least one forensic quality finger print of the mother, and
c) the at least one identification parameter of the mother;

select, in real-time, a sharpest forensic quality foot print for each foot of the infant from the plurality of forensic quality foot prints of the infant;

generate, in real-time, a single encrypted infant identification data file, comprising:
a) the sharpest forensic quality foot print for each foot of the infant,
b) the at least one forensic quality finger print of the mother,
c) the at least one identification parameter of the mother, and
d) the at least one customer identification number; and cause to generate at least one infant identification output based, at least in part, on the single encrypted infant identification data file.

2. The system of claim 1, further comprising:
a specifically programmed forensic quality printer configured to produce forensic quality hardcopy images,
wherein the forensic quality hardcopy images maintain sharpness and detail rendition of the identifiable friction ridge minutiae up to at least 4× magnification.

3. The system of claim 1, wherein the system is configured to electronically compare at least one first forensic quality foot print of the infant captured by the specialized forensic quality scanner at a first time point with at least one second forensic quality foot print of the infant captured by the specialized forensic quality scanner captured at a second time point to determine the at least one sharpest forensic quality foot print of the infant.

4. The system of claim 1, wherein the first software, the second software, or both are further configured to:

for each forensic quality foot print of the infant, extract, in real-time, ridge detail within a predetermined area of such forensic quality foot print of the infant;

create, in real-time, at least one digital topographic representation of such forensic quality foot print of the infant based, at least in part, on the ridge detail; and match, in real-time, the at least one digital topographic representation of such forensic quality foot print of the infant to at least one other digital topographic representation of at least one other foot print of at least one other infant.

5. The system of claim 1, wherein the at least one identification parameter comprises: at least one email address of the mother, at least one cell phone number of the mother, at least one home phone number of the mother, at least one address of the mother, at least one password provided by the mother, or any combination thereof.

6. The system of claim 1, wherein the at least one infant identification output is at least one of: at least one forensic quality printout, or at least one forensic quality graphical image shown on a screen of at least one input/output device.

7. The system of claim 6, wherein the at least one forensic quality printout is a keepsake personalized with information related to a facility in which the infant has been delivered.

8. A computer method, comprising:
capturing, by a specialized forensic quality scanner:
  i) a plurality of forensic quality foot prints of an infant at a birth time, and
  ii) at least one forensic quality finger print of a mother of the infant,
wherein the specialized forensic quality scanner comprises:
  i) a scanning unit, and
  ii) a computer, storing first software and having a visual display;
wherein, when executing the first software, the computer is configured to generate a graphical user interface having at least one designated area to display a foot print of the infant when a foot of the infant touches a scanning surface of the scanning unit before an operator of the specialized forensic quality scanner activates the scanning unit to capture the plurality of forensic quality foot prints of the infant based on a visual appearance of the foot print within the at least one designated area;
wherein the plurality of forensic quality foot prints of the infant has a forensic quality that is achieved when:
each respective foot print of the infant has an identifiable friction ridge minutiae, allowing to electronically differentiate the infant from another infant based on respective identifiable friction ridge minutiae,
at least 80% of the forensic quality foot prints have a gray-scale dynamic range of at least 200 gray-levels, and
at least 99% of the plurality of forensic quality foot prints have a dynamic range of at least 128 gray-levels;

receiving, in real-time, at least one identification parameter of the mother;

generating, in real-time, at least one customer identification number and associating, in real-time, the at least one customer identification number with:
a) the plurality of forensic quality foot prints of the infant,
b) the at least one forensic quality finger print of the mother, and
c) the at least one identification parameter of the mother;

selecting, in real-time, a sharpest forensic quality foot print for each foot of the infant from the plurality of forensic quality foot prints of the infant;

generating, in real-time, a single encrypted infant identification data file, comprising:
- a) the sharpest forensic quality foot print for each foot of the infant,
- b) the at least one forensic quality finger print of the mother,
- c) the at least one identification parameter of the mother, and
- d) the at least one customer identification number; and causing to generate at least one infant identification output based, at least in part, on the single encrypted infant identification data file.

9. The method of claim 8, further comprising:

producing, by a specifically programmed forensic quality printer, forensic quality hardcopy images; and wherein the forensic quality hardcopy images maintain sharpness and detail rendition of the identifiable friction ridge minutiae up to at least 4× magnification.

10. The method of claim 8, wherein the method further comprises:

electronically comparing at least one first forensic quality foot print of the infant captured by the specialized forensic quality scanner at a first time point with at least one second forensic quality foot print of the infant captured by the specialized forensic quality scanner captured at a second time point to determine the at least one sharpest forensic quality foot print of the infant.

11. The method of claim 8, further comprising:

extracting, in real-time, from each forensic quality foot print of the infant, ridge detail within a predetermined area of such forensic quality foot print of the infant, creating, in real-time, at least one digital topographic representation of such forensic quality foot print of the infant based, at least in part, on ridge detail; and matching, in real-time, the at least one digital topographic representation of such forensic quality foot print of the infant to at least one other digital topographic representation of at least one other foot print of at least one other infant.

12. The method of claim 8, wherein the at least one identification parameter comprises: at least one email address of the mother, at least one cell phone number of the mother, at least one home phone number of the mother, at least one address of the mother, at least one password provided by the mother, or any combination thereof.

13. The method of claim 8, wherein the at least one infant identification output is at least one of: at least one forensic quality printout, or at least one forensic quality graphical image shown on a screen of at least one input/output device.

14. The method of claim 13, wherein the at least one forensic quality printout is a keepsake personalized with information related to a facility in which the infant has been delivered.

* * * * *